(12) United States Patent
Kenyon et al.

(10) Patent No.: US 11,293,453 B2
(45) Date of Patent: Apr. 5, 2022

(54) POSITIVE AIRWAY PRESSURE DEVICE INCLUDING BLOWER AND SUPPORT SYSTEM THEREFOR

(71) Applicant: ResMed Motor Technologies Inc, Chatsworth, CA (US)

(72) Inventors: Barton John Kenyon, Sydney (AU); David B. Sears, Woodland Hills, CA (US); Aleksandr S. Nagorny, Canoga Park, CA (US); Samuel Aziz Mebasser, Chatsworth, CA (US); Peter John Sweeney, Sydney (AU)

(73) Assignee: ResMed Motor Technologies Inc, Chatsworth, CA (US)

( * ) Notice: Subject to any disclaimer, the term of this patent is extended or adjusted under 35 U.S.C. 154(b) by 345 days.

(21) Appl. No.: 16/504,531

(22) Filed: Jul. 8, 2019

(65) Prior Publication Data

US 2019/0334418 A1 Oct. 31, 2019

Related U.S. Application Data

(63) Continuation of application No. 14/136,399, filed on Dec. 20, 2013, now Pat. No. 10,396,640, which is a
(Continued)

(51) Int. Cl.
*F04D 29/40* (2006.01)
*F04D 29/08* (2006.01)
(Continued)

(52) U.S. Cl.
CPC ......... *F04D 29/403* (2013.01); *F04D 17/165* (2013.01); *F04D 25/082* (2013.01);
(Continued)

(58) Field of Classification Search
CPC .... F04D 29/403; F04D 29/602; F04D 29/603; F04D 29/083; F04D 17/165; F04D 25/12; F04D 25/082
See application file for complete search history.

(56) References Cited

U.S. PATENT DOCUMENTS 2,401,386 A    2/1942  Smellie
2,670,896 A *  3/1954  Ardito ...................... A47L 9/22
                                                    417/363
(Continued)

FOREIGN PATENT DOCUMENTS

CN    1068400 A    1/1993
CN    1441986 A    9/2003
(Continued)

OTHER PUBLICATIONS

Notification of the Third Office Action dated Sep. 27, 2019 in Chinese Application No. 201610811736.6, with English translation, 16 pages.
(Continued)

*Primary Examiner* — Charles G Freay
(74) *Attorney, Agent, or Firm* — Nixon & Vanderhye P.C.

(57) ABSTRACT

A blower includes a stationary portion including an inlet and an outlet, a rotating portion provided to the stationary portion, and a motor adapted to drive the rotating portion. The inlet and outlet are co-axially aligned. The stationary portion includes a housing, a stator component provided to the housing, and a tube providing an interior surface. The rotating portion includes one or more bearings that are provided along the interior surface of the tube to support a rotor within the tube. In an embodiment, the blower is structured to supply air at positive pressure.

7 Claims, 32 Drawing Sheets

Related U.S. Application Data continuation of application No. 12/155,528, filed on Jun. 5, 2008, now Pat. No. 8,636,479.

(60) Provisional application No. 60/924,909, filed on Jun. 5, 2007, provisional application No. 60/996,001, filed on Oct. 24, 2007, provisional application No. 61/064,477, filed on Mar. 7, 2008.

(51) Int. Cl.
| | |
|---|---|
| *F04D 29/60* | (2006.01) |
| *F04D 25/08* | (2006.01) |
| *F04D 25/12* | (2006.01) |
| *H02K 1/18* | (2006.01) |
| *H02K 3/52* | (2006.01) |
| *H02K 5/08* | (2006.01) |
| *H02K 5/128* | (2006.01) |
| *H02K 5/173* | (2006.01) |
| *H02K 5/22* | (2006.01) |
| *H02K 5/24* | (2006.01) |
| *H02K 7/08* | (2006.01) |
| *H02K 7/14* | (2006.01) |
| *H02K 9/14* | (2006.01) |
| *F04D 17/16* | (2006.01) |
| *A61M 16/12* | (2006.01) |
| *A61M 16/00* | (2006.01) |
| *F04D 25/06* | (2006.01) |
| *F04D 29/059* | (2006.01) |
| *H02K 15/04* | (2006.01) |

(52) U.S. Cl.
CPC ........... *F04D 25/12* (2013.01); *F04D 29/083* (2013.01); *F04D 29/602* (2013.01); *F04D 29/603* (2013.01); *H02K 1/185* (2013.01); *H02K 3/522* (2013.01); *H02K 5/08* (2013.01); *H02K 5/128* (2013.01); *H02K 5/1732* (2013.01); *H02K 5/225* (2013.01); *H02K 5/24* (2013.01); *H02K 7/083* (2013.01); *H02K 7/14* (2013.01); *H02K 9/14* (2013.01); *A61M 16/0066* (2013.01); *A61M 16/122* (2014.02); *A61M 2202/0208* (2013.01); *A61M 2205/3368* (2013.01); *A61M 2205/42* (2013.01); *F04D 25/0606* (2013.01); *F04D 29/059* (2013.01); *H02K 15/0435* (2013.01); *H02K 2205/09* (2013.01); *H02K 2213/03* (2013.01); *Y10T 29/49009* (2015.01)

(56) References Cited

U.S. PATENT DOCUMENTS

| | | | |
|---|---|---|---|
| 3,243,102 A | 3/1966 | McMahan | |
| 3,877,142 A | 4/1975 | Hamano | |
| 4,245,965 A | 1/1981 | Brown | |
| 4,866,324 A | 9/1989 | Yuzawa | |
| 4,978,281 A * | 12/1990 | Conger, IV | F04D 25/082 |
| | | | 264/271.1 |
| 5,099,182 A | 3/1992 | Isaacson et al. | |
| 5,168,186 A | 12/1992 | Yashiro | |
| 5,343,104 A | 8/1994 | Takahashi et al. | |
| 5,474,429 A | 12/1995 | Heidelberg et al. | |
| 5,555,956 A | 9/1996 | Voss et al. | |
| 5,610,461 A | 3/1997 | Dohogne et al. | |
| 5,692,886 A | 12/1997 | Kobayashi et al. | |
| 5,714,827 A | 2/1998 | Hansson | |
| 5,851,174 A | 12/1998 | Jarvik | |
| 6,018,208 A | 1/2000 | Maher et al. | |
| 6,045,340 A | 4/2000 | Batchelder et al. | |
| 6,111,334 A | 8/2000 | Horski et al. | |
| 6,129,524 A | 10/2000 | Woollenweber et al. | |
| 6,229,240 B1 | 5/2001 | Kech | |
| 6,232,690 B1 | 5/2001 | Schmider | |
| 6,296,459 B1 | 10/2001 | Saputo et al. | |
| 6,309,180 B1 | 10/2001 | Gilliland et al. | |
| 6,365,998 B1 | 4/2002 | Kech et al. | |
| 6,386,845 B1 | 5/2002 | Bedard | |
| 6,472,782 B1 | 10/2002 | Selci | |
| 6,629,528 B1 | 10/2003 | Wickham et al. | |
| 7,037,084 B2 | 5/2006 | King | |
| 7,048,250 B2 | 5/2006 | McCarthy | |
| 7,059,345 B2 * | 6/2006 | Shaw | G05D 16/208 |
| | | | 137/565.35 |
| 7,096,864 B1 | 8/2006 | Mayer et al. | |
| 7,098,565 B2 | 8/2006 | Lee | |
| 7,448,383 B2 | 11/2008 | Delache et al. | |
| D619,700 S | 7/2010 | Kenyon et al. | |
| 7,866,944 B2 | 1/2011 | Kenyon et al. | |
| 2001/0033742 A1 | 10/2001 | Weaver et al. | |
| 2002/0000228 A1 | 1/2002 | Schoeb | |
| 2002/0074895 A1 | 6/2002 | Klode | |
| 2003/0062045 A1 | 4/2003 | Woodring et al. | |
| 2003/0146671 A1 | 8/2003 | Diehl et al. | |
| 2003/0168064 A1 | 9/2003 | Daly et al. | |
| 2004/0191052 A1 | 9/2004 | King | |
| 2005/0012411 A1 | 1/2005 | Hoffman et al. | |
| 2005/0217673 A1 | 10/2005 | Daly et al. | |
| 2006/0017339 A1 | 1/2006 | Chordia et al. | |
| 2006/0191531 A1 | 8/2006 | Mayer et al. | |
| 2006/0237005 A1 | 10/2006 | Virr et al. | |
| 2007/0013242 A1 | 1/2007 | Tung et al. | |
| 2007/0052318 A1 | 3/2007 | Marioni | |
| 2007/0080604 A1 | 4/2007 | Yang et al. | |
| 2008/0178879 A1 | 7/2008 | Roberts et al. | |
| 2008/0304986 A1 | 12/2008 | Kenyon et al. | |
| 2010/0059056 A1 | 3/2010 | Sears et al. | |
| 2010/0132711 A1 | 6/2010 | Kenyon | |
| 2011/0037352 A1 | 2/2011 | Lin et al. | |
| 2014/0101926 A1 | 4/2014 | Kenyon et al. | |

FOREIGN PATENT DOCUMENTS

| | | |
|---|---|---|
| CN | 1448004 A | 10/2003 |
| CN | 1523736 A | 8/2004 |
| CN | 2831598 Y | 10/2006 |
| CN | 2852503 | 12/2006 |
| DE | 2 325 473 A1 | 12/1974 |
| DE | 38 18 532 A1 | 12/1989 |
| DE | 19626896 A1 | 1/1998 |
| DE | 198 45 864 A1 | 4/2000 |
| DE | 102 04 037 A1 | 8/2003 |
| EP | 546 508 A1 | 6/1993 |
| EP | 0530786 B1 | 5/1995 |
| JP | 52-135011 | 11/1977 |
| JP | 55-63557 | 5/1980 |
| JP | 62-107650 A | 5/1987 |
| JP | S63-209445 | 8/1988 |
| JP | H7-203657 | 8/1995 |
| JP | H10-127000 | 5/1998 |
| JP | 10-336948 | 12/1998 |
| JP | 2000-14110 | 1/2000 |
| JP | 2000-184657 | 6/2000 |
| JP | 2002-54590 | 2/2002 |
| JP | 2002-276647 | 9/2002 |
| JP | 2003-189522 A | 7/2003 |
| JP | 2004-242444 | 8/2004 |
| JP | 2005-69116 A | 3/2005 |
| JP | 2006-527324 | 11/2006 |
| JP | 2006-348913 A | 12/2006 |
| JP | 2007-113874 A | 5/2007 |
| JP | 2007-196363 | 8/2007 |
| JP | 2009-513192 | 4/2009 |
| WO | 2004/112873 | 12/2004 |
| WO | PCT/AU2006/001617 | 10/2006 |
| WO | WO 2007/045017 A2 | 4/2007 |
| WO | 2007/048205 | 5/2007 |

(56) References Cited

FOREIGN PATENT DOCUMENTS

WO  PCT/AU2007/000719    5/2007
WO  WO 2008/051534       5/2008

OTHER PUBLICATIONS

Notification of the Fifth Office Action dated Dec. 8, 2020 in Chinese Application No. 201610811736.6, with English translation, 16 pages.
Notice of Reasons for Rejection dated Jan. 12, 2021 in Japanese Application No. 2019-209594, with English translation, 8 pages.
Chinese Decision of Rejection dated Jun. 11, 2020 in Chinese Application No. 201610811736.6, with English translation, 12 pages.
U.S. Appl. No. 60/853,778, filed Oct. 2006, Sears.
U.S. Appl. No. 60/877,373, filed Dec. 2006, Suzuki et al.
U.S. Appl. No. 60/929,558, filed Jul. 2007, Sears.
Examination Report issued in New Zealand Patent Appl. No. 568932, dated Oct. 15, 2009.
Examination Report issued in European Patent App. No. 08157685.2, (dated Apr. 7, 2010).
Examination Report issued in related New Zealand Patent Appl. No. 579429 (dated Jan. 11, 2011).
Office Action issued in related Chinese Patent Appl. No. 200810131444.3 (dated May 25, 2011) with English translation.
Chinese Office Action issued in related Application No. 200810131444.3 (dated Mar. 15, 2012).
Office Action issued in a corresponding Chinese Application No. 200810131444.3 (dated Aug. 23, 2012) with English translation thereof.
Patent Examination Report issued in a corresponding Australian Appl. No. 2008202487, dated Aug. 27, 2012.
Decision of Rejection issued in a corresponding Chinese Appl. No. 200810131444.3 with English translation thereof, dated Apr. 2, 2013.
Office Action issued in a corresponding Japanese Appl. No. 2008-147245, dated Jun. 4, 2013, with English language translation thereof.
Office Action issued in corresponding Chinese Appln. No. 201310301043.9 dated Mar. 6, 2015 with English translation thereof.
Office Action issued in corresponding Japanese Application No. 2014-014172 dated Jun. 29, 2015, with English translation thereof.
Second Office Action issued in corresponding Chinese Application No. 201310301043.9 dated Aug. 11, 2015, with English translation thereof.
Patent Examination Report No. 1 issued in corresponding Australian Application No. 2013231018 dated Sep. 21, 2015.
Patent Examination Report No. 2 issued in corresponding Australian Appln. No. 2013231018 dated Dec. 11, 2015.
Notice of Allowance issued in corresponding Japanese Appln. No. 2014-014172 dated Dec. 14, 2015, with English translation thereof.
Patent Examination Report No. 3 issued in corresponding Australian Patent Application No. 2013231018 dated Jun. 29, 2016.
Office Action dated Dec. 26, 2016 issued in Japanese Application No. 2016-003316 with English translation (12 pages).
Office Action dated Aug. 4, 2017 issued in the European Application No. 08 157 685.2 (5 pages).
Office Action dated Aug. 13, 2018 issued in Japanese Application No. 2017-175571 with English translation (8 pages).
Office Action dated Aug. 28, 2018 issued in Chinese Application No. 2016108117366 with English translation (18 pages).
Extended European Search Report dated Mar. 13, 2019 in European Application No. 18206950.0, 7 pages.

\* cited by examiner

POSITIVE AIRWAY PRESSURE DEVICE INCLUDING BLOWER AND SUPPORT SYSTEM THEREFOR

CROSS-REFERENCE TO APPLICATION

This application is a continuation of U.S. patent application Ser. No. 14/136,399, filed Dec. 20, 2013, which is a continuation of U.S. patent application Ser. No. 12/155,528, filed Jun. 5, 2008, now U.S. Pat. No. 8,636,479, which claims the benefit of U.S. Provisional Application Nos. 60/924,909, filed Jun. 5, 2007, 60/996,001, filed Oct. 24, 2007, and 61/064,477, filed Mar. 7, 2008, each of which are incorporated herein by reference in their entirety.

FIELD OF THE INVENTION

The present invention relates to a blower for generating a pressure differential (e.g., air at positive or negative (vacuum) pressure). In an embodiment, the blower may be used in a positive airway pressure (PAP) device or flow generator used for the delivery of respiratory therapy to a patient. Examples of such therapies are Continuous Positive Airway Pressure (CPAP) treatment, Non-Invasive Positive Pressure Ventilation (NIPPV), and Variable Positive Airway Pressure (VPAP). The therapy is used for treatment of various respiratory conditions including Sleep Disordered Breathing (SDB) and more particularly Obstructive Sleep Apnea (OSA). However, the blower may be used in other applications (e.g., vacuum applications (medical or otherwise)).

BACKGROUND OF THE INVENTION

Blowers generally include two main parts: a rotating part, namely an impeller and shaft; and a stationary part that defines a fluid flow path, typically a chamber such as a volute.

Bearings are usually employed in pairs and in coaxial arrangements to support the rotating part, e.g., shaft. Ideally, the two bearings are located by a stationary member that constrains the two bearings in perfect axial alignment. Real world designs are less than perfect and, therefore, compromise bearing performance.

A widely employed bearing suspension mode involves holding each bearing within a separate housing structure and fitting those housing structures together to approximate a coaxial bearing arrangement.

There are two main classes of constraints on the packaging of bearings. One constraint relates to the practical limits of manufacturing precision, and another constraint relates to the need to attach and efficiently package items that must rotate.

With respect to the first constraint, although the precision of part forming technologies improves continuously, the state of the art is far from perfect. Furthermore, increased precision usually translates to greater expense, often dissuading a manufacturer from embracing the state of the art processes.

The second constraint is driven by the need to place items (such as a rotor/stator) between bearing pairs. This typically leads to the use of a two part housing construction. A consequence of multipart housings is that they accumulate unwanted tolerance build-up at each faying or joint surface, and, as such, each component part must be precisely shaped so that the accumulated dimensional errors remain within acceptable range.

Thus, a need has developed in the art for an improved arrangement that does not suffer from the above-mentioned drawbacks.

SUMMARY OF THE INVENTION

One aspect of the invention relates to a blower including a stationary portion including an inlet and an outlet, a rotating portion provided to the stationary portion (e.g., in close proximity to, but not touching), and a motor (e.g., electric motor) adapted to drive the rotating portion. The inlet and outlet are co-axially aligned. The stationary portion includes a housing, a stator component provided to the housing, and a tube providing an interior surface. The rotating portion includes one or more bearings that are provided along the interior surface of the tube to support a rotor within the tube (e.g., bearings connect the rotating portion to the stationary portion). In an alternative embodiment, the stator component may include stator vanes, and the stator vanes may be a separate part to the tube. In an embodiment, the blower is structured to supply air at positive pressure. In an embodiment, the stator component and/or tube may be constructed of a plastic material.

Another aspect of the invention relates to a PAP device for generating a supply of pressurized gas to be provided to a patient for treatment. The PAP device includes an outer casing, a blower, and a support system provided between the blower and the outer casing. The support system includes an annular seal provided to an outer surface of the blower and adapted to engage the outer casing to support the blower within the casing and separate an inlet side of the blower from an outlet side of the blower. In an alternative embodiment, the annular seal may be overmolded to the blower or may be a separate part that is adapted to be attached to the blower.

Another aspect of the invention relates to a method for forming windings of a stator assembly in a blower. The method includes providing a stationary portion for the blower including a tube adapted to support a rotor, and using the tube as a mandrel to form the windings of the stator assembly.

Another aspect of the invention relates to a blower including a stationary portion including an inlet and an outlet, a rotating portion provided to the stationary portion, and a motor adapted to drive the rotating portion. The stationary portion includes a housing and a stator component provided to the housing. The stator component includes a portion adapted to support a rotor of the rotating portion and a cage that surrounds the portion. In an embodiment, the blower is structured to supply air at positive pressure. In an embodiment, the stator component may be constructed of a plastic material. In an embodiment, the portion includes a tube and the motor includes a stator assembly that is provided along an exterior surface of the tube. In an alternative embodiment, the portion includes a metal bearing support having first and second parts adapted to support first and second bearings that support the rotor.

Another aspect of the invention relates to a blower including a stationary portion including an inlet and an outlet, a rotating portion provided to the stationary portion, a motor adapted to drive the rotating portion and including a stator assembly with windings, and a detection system to detect faults in the motor by monitoring resistance of the windings and/or current draw and then providing a signal to indicate detected faults in the motor. In an embodiment, the blower is structured to supply air at positive pressure.

Another aspect of the invention relates to a stator (e.g., one or two or more part magnetic core) for a stator assembly. The stator includes an inner portion including a plurality of stator teeth and a ring-shaped outer portion structured to receive the inner portion. The outer portion includes a plurality of recesses along its inner circumference adapted to receive respective teeth of the inner portion.

Another aspect of the invention relates to a blower including a stationary portion including an inlet and an outlet, a rotating portion provided to the stationary portion, and a motor adapted to drive the rotating portion. The inlet and outlet are co-axially aligned. The stationary portion includes a housing and a metal bearing support provided to the housing. The metal bearing support includes first and second parts and the rotating portion includes first and second bearings that are supported by the respective first and second parts to support a rotor within the metal bearing support. In an embodiment, the blower is structured to supply air at positive pressure.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1-2 is a perspective view of a stator vane/cover component of the blower shown in FIG. 1-1;

FIG. 1-3 is a perspective view of a vaned shield of the blower shown in FIG. 1-1;

FIG. 1-4 is a top view of the blower shown in FIG. 1-1 with a blower housing cover removed;

FIG. 2 is a cross-sectional view of a blower according to another embodiment of the present invention;

FIG. 3 is a cross-sectional view of a blower according to another embodiment of the present invention;

FIG. 4 is a cross-sectional view of a blower according to another embodiment of the present invention;

FIG. 6-1 is a partial cross-sectional view of a sealing arrangement for a blower according to an embodiment of the present invention;

FIG. 6-2 is a partial cross-sectional view of a sealing arrangement for a blower according to another embodiment of the present invention;

FIG. 7-1 is a perspective view of a blower according to another embodiment of the invention;

FIG. 7-2 is a side view of the blower shown in FIG. 7-1;

FIG. 7-3 is a cross-sectional view of the blower shown in FIG. 7-1;

FIG. 7-4 is an enlarged portion of the cross-sectional view shown in FIG. 7-3;

FIG. 7-4B is an enlarged portion of a blower in cross-section according to another embodiment of the present invention;

FIG. 7-5 is another cross-sectional view of the blower shown in FIG. 7-1;

FIG. 7-6 is an enlarged portion of the cross-sectional view shown in FIG. 7-5;

FIG. 7-7 is a side view of the blower shown in FIG. 7-1 with a housing removed;

FIG. 7-8 is a top perspective view of a stator component of the blower shown in FIG. 7-1;

FIG. 7-9 is a bottom perspective view of the stator component shown in FIG. 7-8;

FIG. 7-10 is a cross-sectional view of the stator component shown in FIG. 7-8;

FIG. 7-11 is a top perspective view of a first shield of the blower shown in FIG. 7-1;

FIG. 7-12 is a top view of the first shield shown in FIG. 7-11;

FIG. 7-13 is a top perspective view of a second shield of the blower shown in FIG. 7-1;

FIG. 8 is a cross-sectional view of a blower according to another embodiment of the present invention;

FIGS. 9-1 to 9-2 are cross-sectional views of a blower according to another embodiment of the present invention;

FIGS. 10-1 to 10-3 are various views of a stator according to an embodiment of the present invention;

FIG. 11 is a plan view of a stator according to another embodiment of the present invention;

FIG. 12-1 is a perspective view of a blower according to another embodiment of the invention;

FIG. 12-2 is a cross-sectional view of the blower shown in FIG. 12-1;

FIG. 12-3 is a perspective view of a stator of the blower shown in FIG. 12-1;

FIG. 13-1 is a perspective view of a blower according to another embodiment of the invention; and FIG. 13-2 is a cross-sectional view of the blower shown in FIG. 13-1.

DETAILED DESCRIPTION OF ILLUSTRATED EMBODIMENTS

Figure 1:
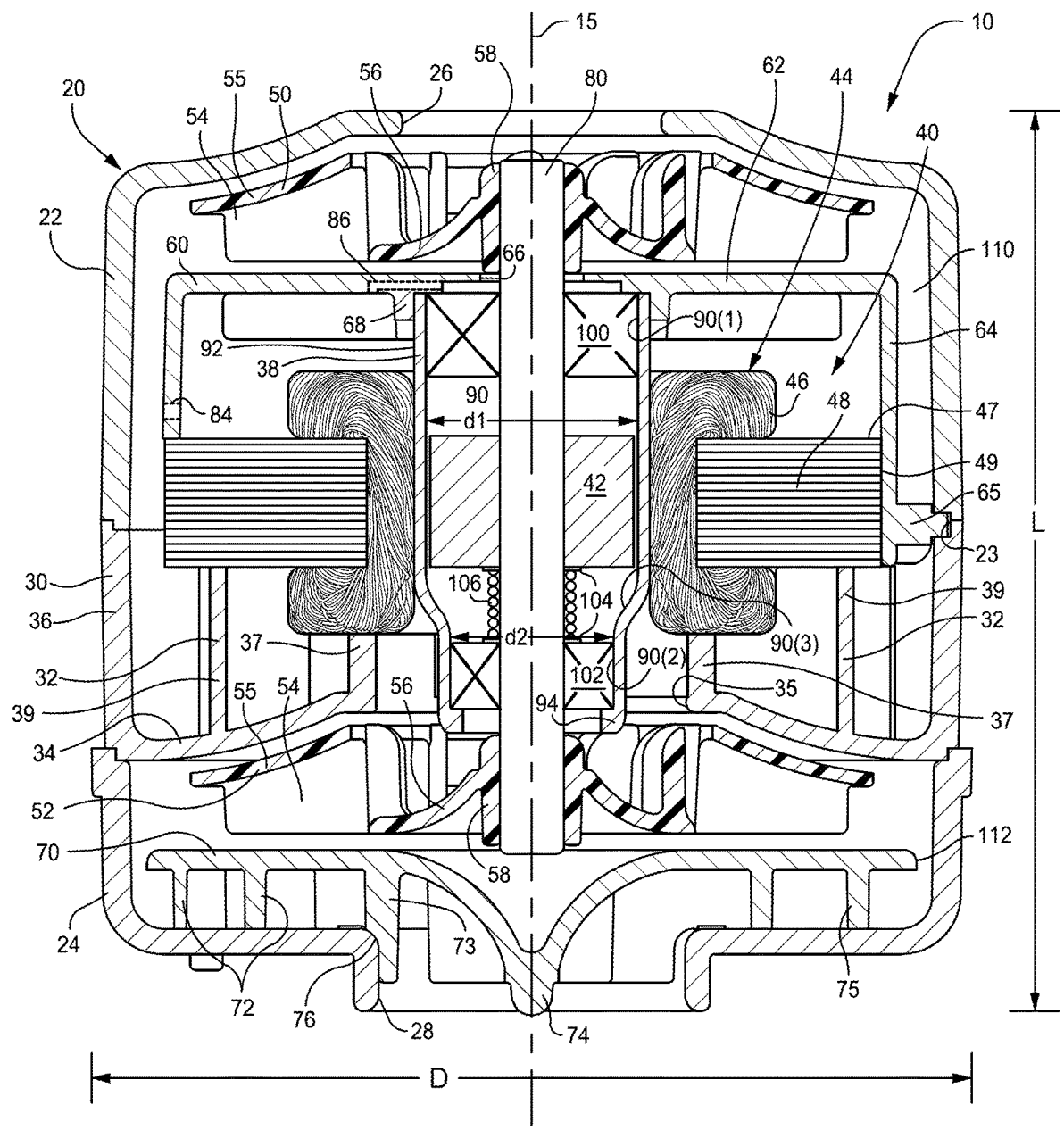
FIG. 1-1 is a cross-sectional view of a blower according to an embodiment of the present invention.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear. Aspects of the invention will be described herein in its application to non-invasive ventilation (NIVV) treatment apparatus (e.g., positive airway pressure (PAP) devices or flow generators), such as CPAP (e.g., in the range of 4-28 cmH$_2$O, at flow rates of up to 180 L/min (measured at the mask)), variable pressure therapy (e.g., low range of 2-6 cmH$_2$O and high range of 6-30 cmH$_2$O), mechanical ventilation and assisted respiration, but it is to be understood that the features of the invention will have application to other fields of application where blowers are used, such as vacuum cleaners, cooling equipment in computers and HVAC devices such as those found in buildings and vehicles. That is, the blowers described herein may have application in both positive pressure and negative pressure applications.

Also, while each blower embodiment below is described as including two stages, it should be appreciated that each embodiment may a single stage design or other multiple stage designs, e.g., three, four, or more stages.

In this specification, the words "air pump" and "blower" may be used interchangeably. In this specification, the phrase "stationary part" may be taken to include "volute". The term "air" may be taken to include breathable gases, for example air with supplemental oxygen. It is also acknowledged that the blowers described herein may be designed to pump fluids other than air.

1. Blower with Bearing Tube

FIGS. 1-1 to 1-4 illustrate a blower 10 according to an embodiment of the present invention. As illustrated, the blower 10 includes two stages with two corresponding impellers 50, 52. In this embodiment, one impeller 50 is positioned on one side of the motor 40 and the other impeller 52 is positioned on the other side of the motor 40. However, other suitable impeller arrangements are possible, e.g., two impellers positioned on the same side of the motor. Also, the blower 10 may include a single stage design or other multiple stage designs, e.g., two or more impellers.

1.1 General Description

A stationary portion of the blower 10 includes a housing 20 with first and second housing parts 22, 24, a stator component 30 including stator vanes 32, and first and second shields 60, 70. A rotating portion of the blower 10 includes a rotatable shaft or rotor 80 adapted to be driven by motor 40 and first and second impellers 50, 52 provided to end portions of the shaft 80. The motor 40 includes a magnet 42 (e.g., two pole magnet) provided to shaft 80 and a stator assembly 44 to cause spinning movement of the shaft 80 via the magnet 42. In an embodiment, the motor may be operated without the use of rotor position sensors, e.g., no Hall sensors on printed circuit board (PCB), which may reduce the number of wires, e.g., 3 wires.

The stator assembly 44 includes windings 46 and a stator or stator lamination stack 48 (e.g., slotless or toothless) provided to the windings 46. Further details of coil winding is disclosed in U.S. Provisional Application No. 60/877,373, filed Dec. 28, 2006, which is incorporated herein by reference in its entirety.

The blower 10 is generally cylindrical and has an inlet 26 provided by the first housing part 22 at one end and an outlet 28 provided by the second housing part 24 at the other end. The blower 10 is operable to draw a supply of gas into the housing 20 through the inlet 26 and provide a pressurized flow of gas at the outlet 28.

The blower 10 has axial symmetry with both the inlet 26 and outlet 28 aligned with an axis 15 of the blower 10. In use, gas enters the blower 10 axially at one end and leaves the blower 10 axially at the other end. Such arrangement may provide relatively low noise in use, e.g., due to axial symmetry and/or low volute turbulence. Exemplary embodiments of such blowers are disclosed in PCT Application No. PCT/AU2007/000719, filed May 24, 2007, which is incorporated herein by reference in its entirety.

In an embodiment, the blower 10 may be relatively compact and have an overall diameter D of about 50-60 mm, e.g., 53 mm, and an overall length L of about 45-55 mm, e.g., 52 mm. However, other suitable sizes are possible.

1.2 Stator Component

Figures 1, 2:
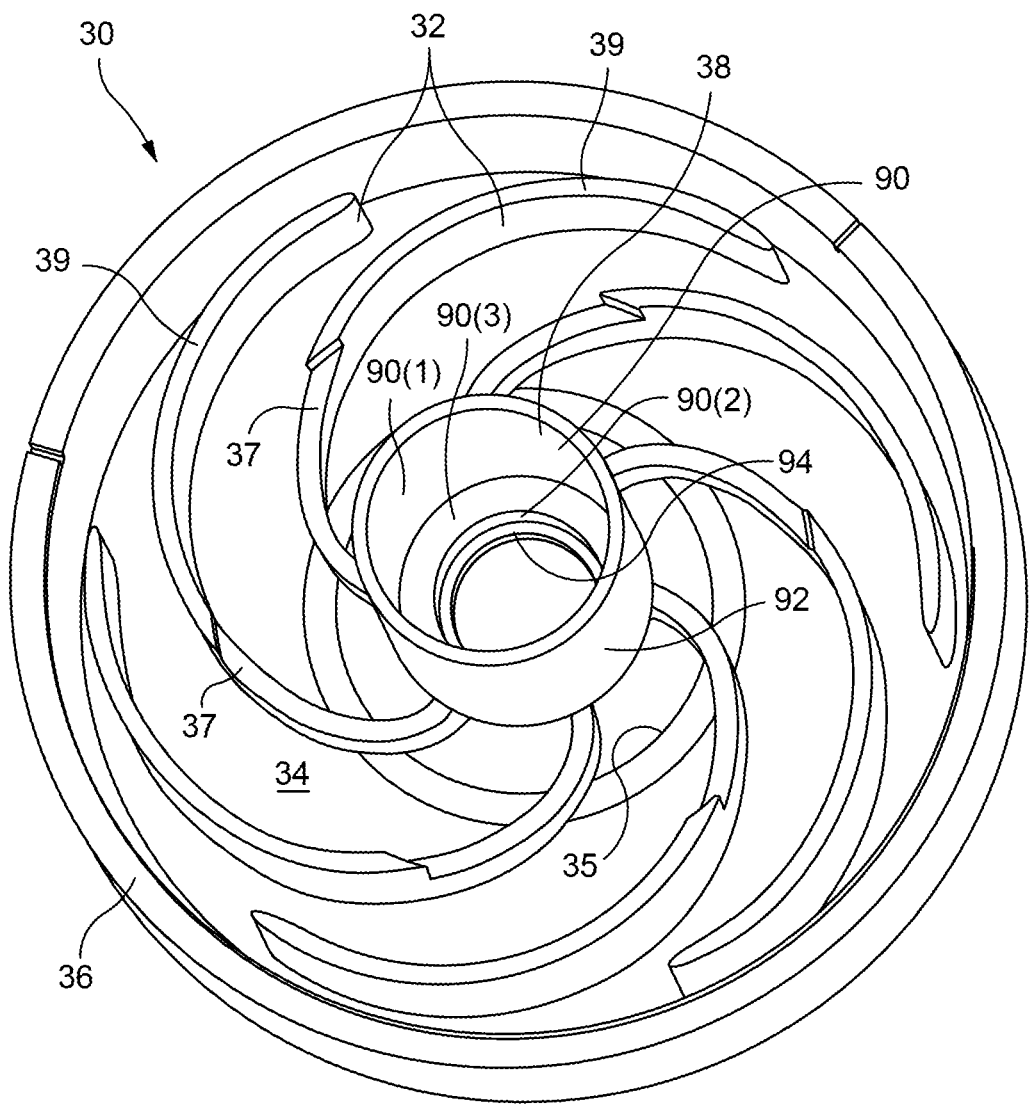

As shown in FIGS. 1-1 and 1-2, the stator component 30 includes a base 34, an annular flange 36 extending from the base 34, a tube or bearing tube 38, and a plurality of stator vanes 32. In the illustrated embodiment, the stator component 30 is integrally formed (e.g., injection molded of plastic material) as a one-piece structure. However, the stator component 30 may be constructed in other suitable manners.

As best shown in FIG. 1-1, the annular flange 36 is sandwiched between the first and second housing parts 22, 24 to support the stator component 30 within the housing 20.

The plurality of stator vanes 32, e.g., between 2 and 100 stator vanes, are structured to direct airflow towards an orifice 35 in the base 34. In the illustrated embodiment, the stator component 30 has six stator vanes 32. Each vane 32 is substantially identical and has a generally spiral shape. In addition, each vane 32 includes an inner portion 37 (adjacent the tube 38) and an outer portion 39. As best shown in FIG. 1-2, the inner portion 37 is recessed (e.g., reduced in height) with respect to the outer portion 39. However, the stator component may have other suitable structure to condition the airflow between stages.

1.2.1 Bearing Alignment and Retention

The interior surface 90 of the tube 38 is structured to retain and align the bearings 100, 102 that rotatably support the shaft 80. In addition, the tube 38 encloses the magnet 42 on the shaft 80, which is aligned in close proximity to the stator assembly 44 provided along an exterior surface 92 of the tube 38. In the illustrated embodiment, the tube 38 has at least a portion that is sufficiently "magnetically transparent" to allow a magnetic field to pass through it, which allows the stator assembly 44 to act on the magnet 42 positioned within the tube 38 without significant loss of flux density and/or increased heat, if any. In an embodiment, such "magnetic transparency" may be provided by one or more of the tube's material properties, e.g., non-electrically conductive, non-magnetic, and/or thermally conductive. For example, the tube may include one or more of the following: anisotropic materials, composite (e.g., base polymers (e.g., LCP and PPS) with either ceramic fillers, graphite fillers, and/or other fillers), heterogeneous fill, insert molding, plating, ion implantation, etc. Alternatively, or in addition, such "magnetic transparency" may be provided by the tube's structural properties, e.g., one or more perforations, slits, etc. in the tube. It should be appreciated that the tube may include one or more of these properties and/or a sufficient degree of these properties to provide sufficient "magnetic transparency." Further details of a magnetically transparent tube are disclosed in U.S. Provisional Application Nos. 60/853,778, filed Oct. 24, 2006, and 60/929,558, filed Jul. 3, 2007, each of which is incorporated herein by reference in its entirety.

In the illustrated embodiment, the tube has a circular cross-sectional configuration along its length. However, it should be appreciated that the tube may have other suitable shapes, e.g., square, polygonal, conical, etc. Also, the tube may include one or more parts, e.g., multi-part construction. In addition, the tube may have different material properties along its length or circumference, e.g., different levels or regions of "magnetic transparency", "non-electrical conductivity", and/or "thermal conductivity."

In the illustrated embodiment, the tube 38 is structured such that mixed bearing sizes may be used. As shown in FIG. 1-1, the upper end of the tube 38 is structured to support bearing 100 and the lower end of the tube 38 is structured to support bearing 102 having a smaller size or diameter than bearing 100.

Specifically, the upper end of the tube 38 includes an annular surface 90(1) defining a diameter d1 and adapted to support bearing 100. The lower end of the tube 38 includes an annular surface 90(2) defining a smaller diameter d2 and adapted to support bearing 102. As illustrated, the one-piece tube 38 provides accurate bore-to-bore alignment which provides accurate bearing-to-bearing alignment.

In an embodiment, the tube may be manufactured such that upper and lower ends of the tube are adapted to support bearings of the same size. However, a tube structured to support mixed bearing sizes may facilitate a line of draw molding process. Also, the tube may be structured to support one or more bearings, and the bearings may include other suitable configurations, e.g., fluid bearings. Further, in an embodiment, the tube may be structured such that the upper end of the tube is structured to support a bearing having a smaller size or diameter than the bearing supported at the lower end of the tube (e.g., blower with a larger inlet diameter to the second impeller).

A sloped surface 90(3) may be provided between surfaces 90(1) and 90(2) to guide the shaft 80 (with bearings 100, 102 provided to respective end portions) into the lower end of the tube 38. For example, the smaller bearing side of the shaft 80 may be inserted into or "dropped into" the tube 38 through the upper end of the tube 38. As the smaller bearing 102 approaches the lower end, the sloped surface 90(3) will guide the bearing 102 into engagement with surface 90(2) having a reduced diameter. Thus, the bearing 102 is self-guided into its operative position.

In the illustrated embodiment, the lower end of the tube 38 includes a flange 94 that provides a stop or support for the bearing 102 at the lower end. The upper end of the tube 38 is adapted to engage the shield or rotor cap 60, which provides a stop for the bearing 100 at the upper end and hence retains the shaft 80 within the tube 38.

Washers 104 and a spring or biasing element 106 may be provided between the bearing 102 and the rotor magnet 42 to maintain alignment of the rotor magnet 42 with the stator assembly 44 and/or provide a pre-load to the inner race of bearing 102.

In an embodiment, end portions of the shaft 80 may include one or more bonding grooves for securing the bearings 100, 102 in an operative position, and an intermediate portion of the shaft 80 may include one or more bonding grooves (e.g., helical bonding grooves) for securing the magnet 42 in an operative position. The bonding grooves may be provided to selected portions of the shaft (e.g., ends and middle of the shaft) or the bonding grooves may extend along the entire length of the shaft. In another embodiment, an intermediate portion of the shaft may include threads (e.g., extending outwardly from the exterior surface of the shaft) for securing the magnet in an operative position.

1.2.2 Stator Assembly Alignment and Retention

The stator assembly 44 is provided along the exterior surface 92 of the tube 38. In addition, the stator component 30 and first shield 60 cooperate to support and maintain the stator assembly 44 in an operative position.

As illustrated, the windings 46 of the stator assembly 44 are encased or supported by the recessed, inner portion 37 of the stator vanes 32, and the stack 48 of the stator assembly 44 is encased or supported by the outer portion 39 of the stator vanes 32. In addition, the shield 60 includes an annular flange 64 that encloses an upper portion of the windings 46 and engages an upper side 47 or an exterior surface 49 of the stack 48 (e.g., left side of FIG. 1-1 shows flange 64 engaging upper side 47 of stack 48 and right side of FIG. 1-1 shows flange 64 engaging exterior surface 49 of stack 48). The elongated portions of the annular flange 64 (i.e., the portions engaging exterior surface 49 of the stack 48) are provided to accommodate tabs that engage the housing as described in greater detail below. Thus, the stator component 30 and shield 60 cooperate to enclose and sandwich the stator assembly 44.

In the illustrated embodiment, the exterior surface 49 of the stack 48 and/or the annular flange 64 engaging the stack 48 is exposed to the flow of gas. This arrangement allows forced-convection cooling of the stack 48 as gas flows through the housing 20 in use. In addition, this arrangement may assist in heating the gas or patient air.

Further, the windings 46 of the stator assembly 44 are exposed to the flow of gas to allow cooling and assist in heating the gas or patient air.

In an embodiment, the stator component 30 and shield 60 may be thermally conductive (e.g., add graphite or other filler to polymer material) to help with heat conduction.

1.3 Shields

The first or upper shield 60 includes a disk portion 62 and the annular flange 64 extending from the outer edge of the disk portion 62 and adapted to engage the stator assembly 44 as described above. The outer edge of the disk portion 62 substantially aligns with or extends radially beyond the outer edge of the impeller 50. The shield 60 provides a narrow annular gap 110 between the annular flange 64 and the side wall of the housing part 22, which is sufficient to direct gas into the stator component 30.

The disk portion 62 includes an opening 66 that allows the shaft 80 to extend therethrough. An annular flange or projection 68 is provided along the opening 66 that is structured to engage the upper end of the tube 38 of the stator component 30, e.g., with a friction fit.

Also, the annular flange 64 includes one or more tabs 65 that are adapted to engage within respective slots 23 defined between the first housing part 22 and the stator component 30 (e.g., see FIGS. 1-1 and 1-4). As shown in FIG. 1-4, the shield 60 includes three tabs 65 that are received in respective slots 23 defined between the first housing part 22 and the stator component 30. However, any suitable number of slots/tabs may be provided. Also, it should be appreciated that the slots/tabs may be optional and the shield 60 may be supported within the housing in other suitable manners.

Figures 1, 2, 3:
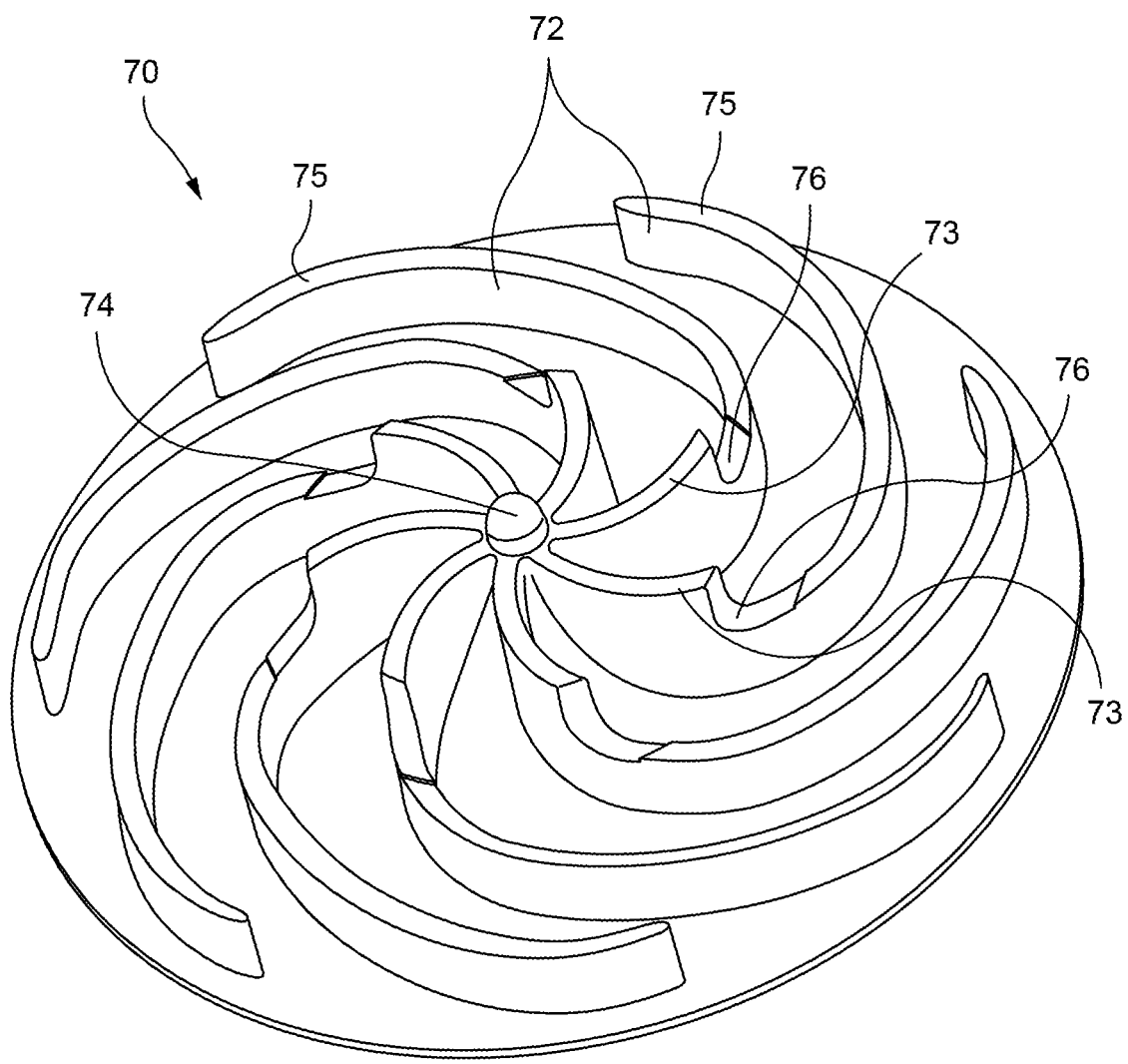

The second or lower shield 70 includes a plurality of stator vanes 72, e.g., between 2 and 100 stator vanes, to direct airflow towards the outlet 28. In the illustrated embodiment, the shield 70 has 7 stator vanes. Each vane 72 is substantially identical and has a generally spiral shape. In addition, each vane 72 includes an inner portion 73 (adjacent the hub 74) and an outer portion 75. As best shown in FIGS. 1-1 and 1-3, the outer portion 75 is recessed (e.g., reduced in height) with respect to the inner portion 73, and a contoured edge 76 extends between the inner and outer portions 73, 75.

In the illustrated embodiment, the stator vanes 72 support the shield 70 within the second housing part 24 adjacent the outlet 28. As illustrated, the contoured edge 76 of the shield 70 engages the edge of the outlet 28 to align the shield 70 with the outlet 28. The hub 74 and inner portion 73 of the vanes 72 extend at least partially through the outlet 28 and the outer portion 75 of the vanes 72 engage the lower wall of the second housing part 24. The hub 74 at the central portion of the shield 70 is shaped to direct the air flow down towards the outlet 28.

1.3.1 Alternative Airflow Path

In an embodiment, the shield 60 may include an inlet conduit 84 and an outlet conduit 86 (as indicated in dashed lines in FIG. 1-1) to provide pressure balance across the bearings 100, 102. Specifically, the inlet and outlet conduits 84, 86 provide a short circuit of pressure around the tube 38 and hence the bearings 100, 102 to avoid such drying out or displacement of the bearings' 100, 102 lubricant (e.g., air flow through the tube and through the interior of the bearings can dry out grease in the bearings and carry away heat from the bearings). That is, the inlet conduit 84 allows air to flow into the space between the shield 60 and the tube 38, and the outlet conduit 86 allows air to flow out of the space. Such arrangement allows any pressure differential to bleed through the inlet and outlet conduits 84, 86, rather than travel through the tube 38 as described above.

In an alternative embodiment, as shown in FIG. 2, grooves 184, 186 may be provided along the shaft 80 to provide a short circuit of airflow or pressure around each of the bearings 100, 102 to avoid drying out of the bearings. As illustrated, the grooves 184, 186 are provided adjacent respective bearings 100, 102 and allow air to flow through the grooves 184, 186 rather than through respective bearings 100, 102, e.g., when air flows through the tube 38 due to pressure differential inside tube 38. In an embodiment, one or more grooves may extend along the length of the shaft, rather than along selected portions as illustrated. Alternatively, the grooves 184, 186 may be on the tube 38 adjacent the outside diameter of respective bearings 100, 102.

1.4 Impellers

In the illustrated embodiment, each impeller 50, 52 includes a plurality of continuously curved or straight blades 54 sandwiched between a pair of disk-like shrouds 55, 56. The shrouds may help to reduce tonal noise in use. The lower shroud 56 incorporates the hub or bushing 58 that is adapted to receive the shaft 80. Also, each impeller 50, 52 includes a tapered configuration wherein the blades 54 taper towards the outer edge. Further details of impellers are disclosed in PCT Application No. PCT/AU2006/001617, filed Oct. 27, 2006, which is incorporated herein by reference in its entirety.

In an embodiment, each impeller may be constructed of glass reinforced polycarbonate. In another embodiment, each impeller may be constructed of glass reinforced liquid crystal polymer (LCP), e.g., Ticona Vectra-E130i. Glass reinforced LCP may improve acoustic dampening, especially with respect to reducing the tonal acoustic noise by reducing the impeller resonating. However, other suitable materials are possible.

1.5 Fluid Flow Path

In the first stage, air enters the blower 10 at the inlet 26 and passes into the first impeller 50 where it is accelerated tangentially and directed radially outward. It is noted that suction is developed at the inlet to draw air into the blower. Air then flows in a spiral manner with a large tangential velocity component and also an axial component passing through the gap 110 defined by the outer edge of the shield 60 and the side wall of housing part 22. As noted above, air may bleed through the shield 60 (through the inlet and outlet conduits 84, 86) to provide pressure balance in use. Air then enters the stator vanes 32 formed in the stator component 30 and is directed radially inwardly towards orifice 35, and thereafter onto the second stage.

In the second stage, air passes into the second impeller 52 where it is accelerated tangentially and directed radially outward. Air then flows in a spiral manner with a large tangential velocity component and also an axial component passing through the gap 112 defined by the outer edge of the shield 70 and the side wall of housing part 24. Air then enters the stator vanes 72 formed in the shield 70 and is directed towards the outlet 28.

In the illustrated embodiment, the airflow enters and exits each stage within the blower in a substantially axial direction. Consequently, the air enters the blower axially at one end, and leaves the blower axially at the other end. The axially symmetric blower provides balance, which leads to lower levels of blade pass tone, and lower levels of turbulence noise.

2. Blower with Mixed Flow Upper Impeller

FIG. 3 illustrates a blower 210 according to another embodiment of the present invention. The blower 210 is substantially similar to the blower 10 described above. In contrast, the upper impeller 250 has a mixed flow configuration and corresponding portions of the first housing part 222 and first shield 260 are tapered to match the mixed flow configuration of the upper impeller 250.

As illustrated, each of the blades 254 of the impeller includes an end portion 257 that tapers toward the outer edge. In addition, the end portion 257 of each blade 254 is bent, angled, or sloped downwardly with respect to the hub 258. For example, a longitudinal axis L of each end portion 257 may be bent or angled at an angle a with respect to an axis H of the hub 258. Such angle a may be about 90°-160°, e.g., 125°. However, other suitable angles are possible depending on application.

The upper wall 225 of the first housing part 222 is tapered to match the mixed flow configuration of the impeller 250, and the upper wall 267 of the shield 260 is tapered to match the mixed flow configuration of the impeller 250.

3. Blower with Alternative Stationary Portion

Figures 1, 2, 3, 4:
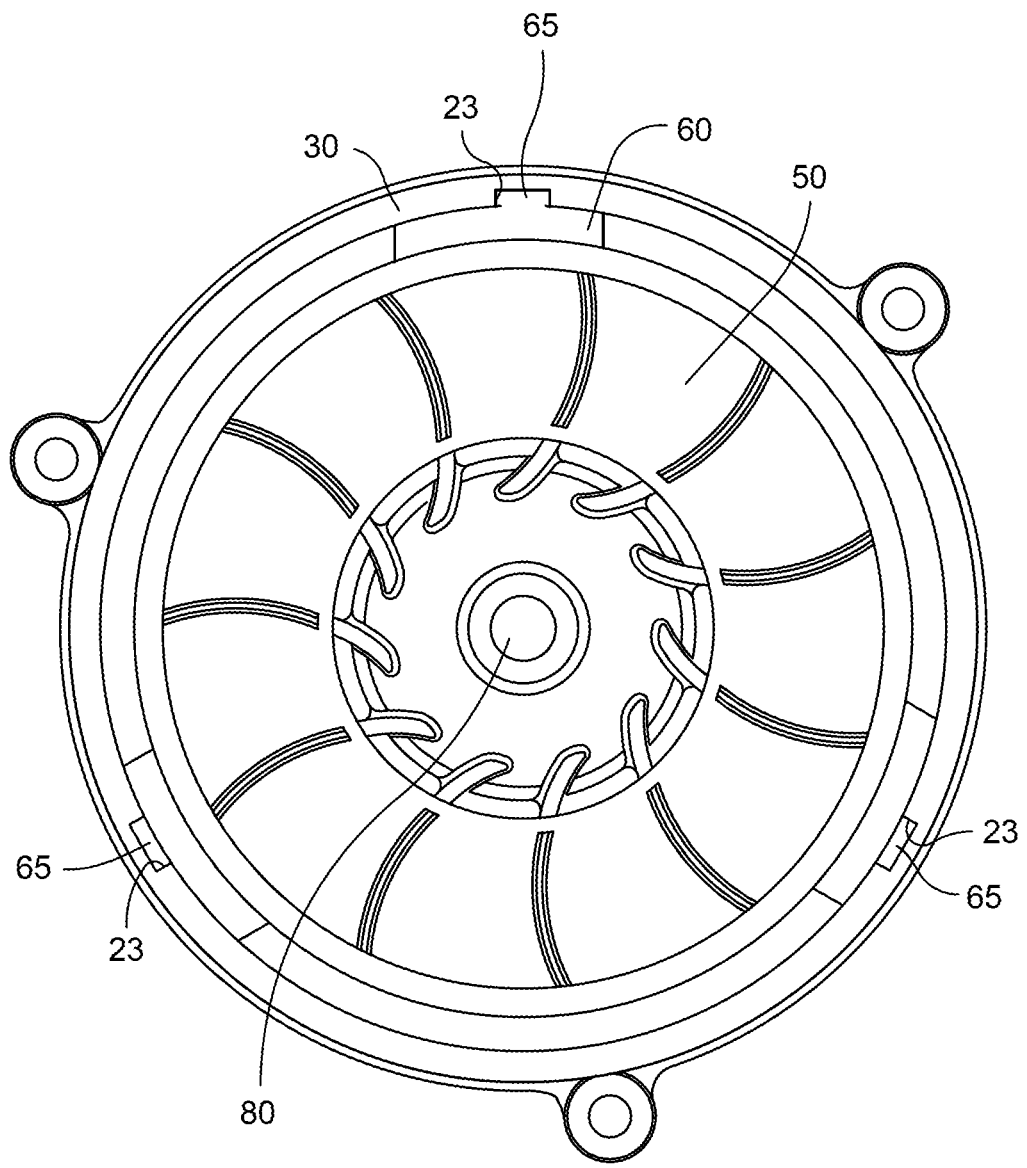
Figure 2:
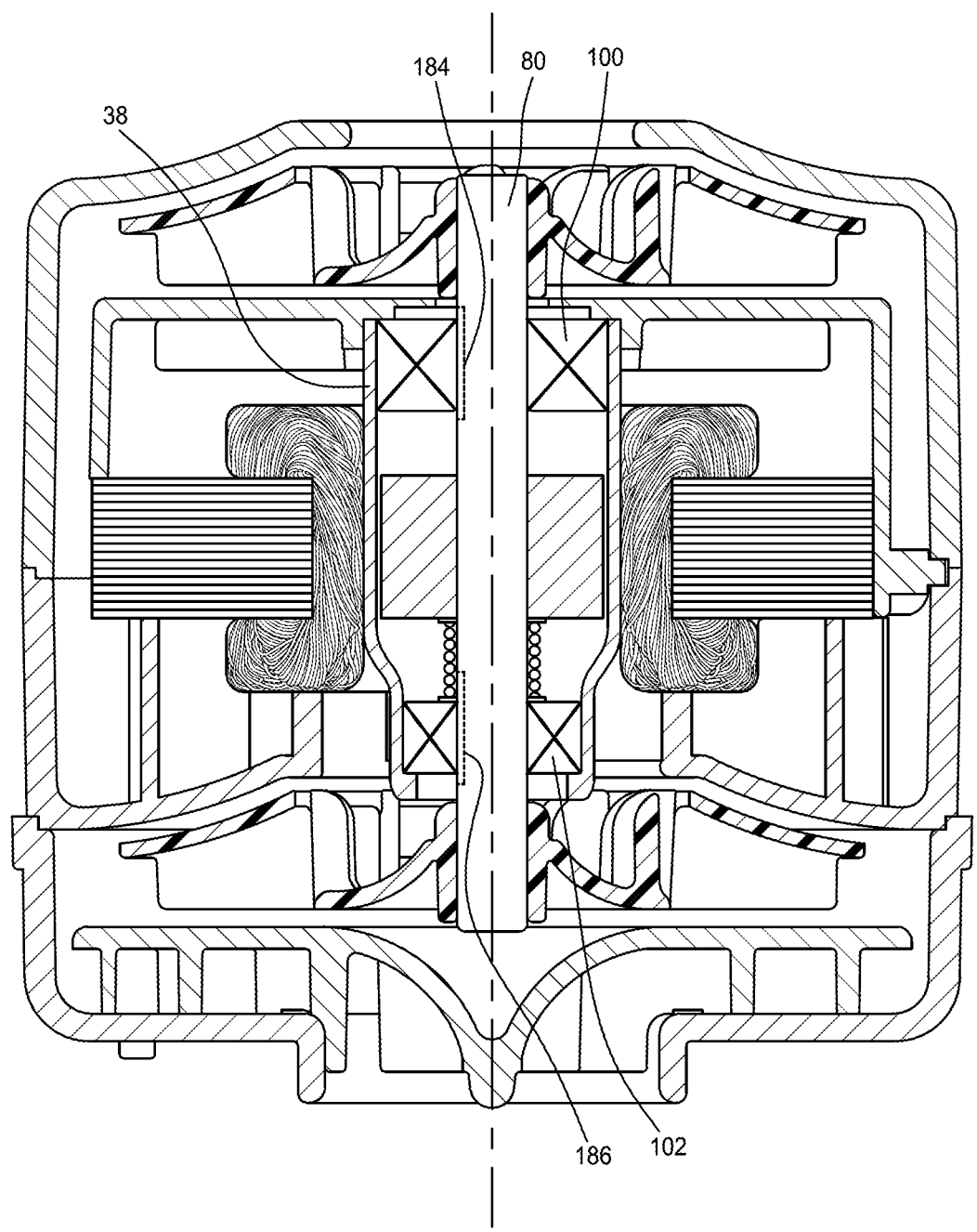
Figure 3:
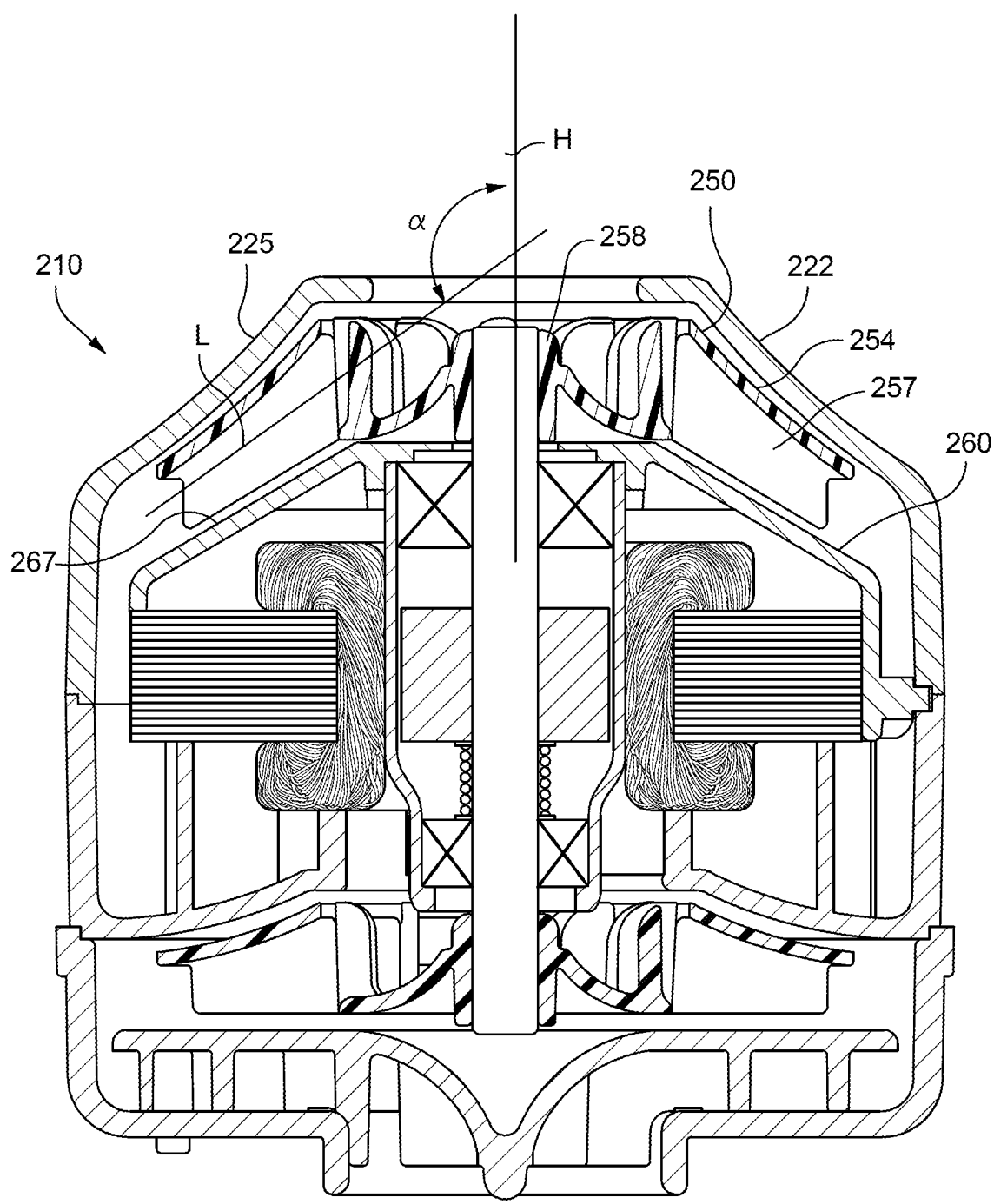
Figure 4:
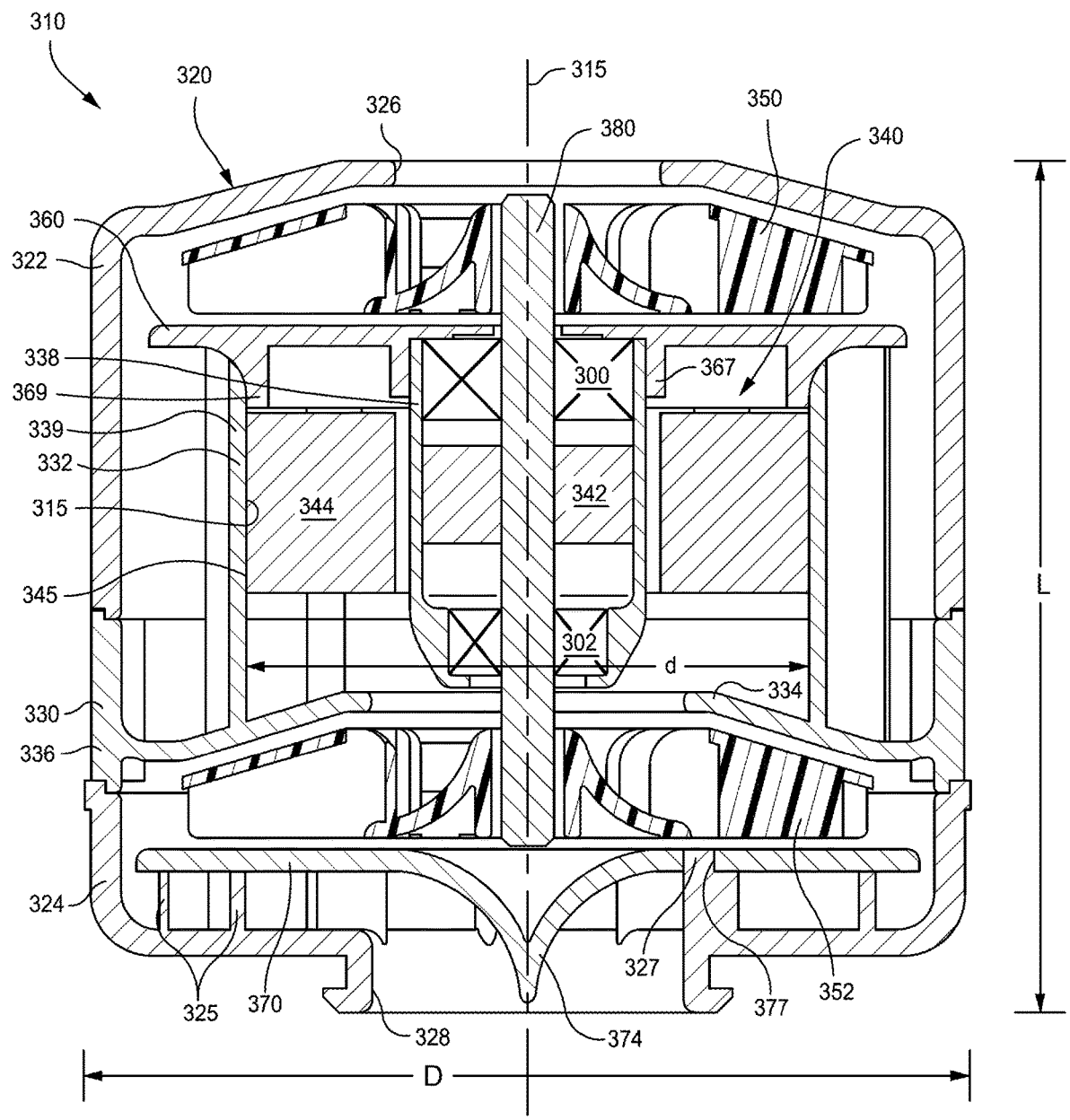

FIG. 4 illustrates a blower 310 according to another embodiment of the present invention. Similar to the blowers 10, 210 described above, the blower 310 includes two stages with one impeller 350 positioned on one side of the motor 340 and one impeller 352 positioned on the other side of the motor 340. Also, the blower 310 has axial symmetry with both the inlet 326 and outlet 328 aligned with an axis 315 of the blower 310. In contrast, the blower 310 provides an alternative arrangement of the stationary portion.

3.1 General Description

A stationary portion of the blower 310 includes a housing 320 with first and second housing parts 322, 324, a stator component 330 including stator vanes 332, and first and second shields 360, 370. A rotating portion of the blower 310 includes a rotatable shaft or rotor 380 adapted to be driven by motor 340 and first and second impellers 350, 352 provided to end portions of the shaft 380. The motor 340 includes a magnet 342 provided to shaft 380 and a stator assembly 344 to cause spinning movement of the shaft 380 via the magnet 342.

In an embodiment, as shown in FIG. 4, the blower 310 may be relatively compact and have an overall diameter D of about 50-60 mm, e.g., 53 mm, and an overall length L of about 45-55 mm, e.g., 52 mm. Each impeller 350, 352 may have a diameter of about 40-45 mm, e.g., 42 mm. However, other suitable sizes are possible.

3.2 Stator Component

As shown in FIG. 4, the stator component 330 includes a base 334, an annular flange 336 extending from the base 334 to support the stator component 330 within the housing 320, a tube 338 to retain and align the bearings 300, 302 that rotatably support the shaft 380, and a plurality of stator vanes 332. Similar to the above embodiments, the stator component 330 may be integrally formed (e.g., injection molded) as a one-piece structure.

In the illustrated embodiment, each vane 332 includes an outer portion 339 that is sufficiently long so that it can support and maintain the stator assembly 344 in an operative position. As illustrated, the outer portion 339 of each vane 332 provides an interior surface 315 that engages an exterior surface 345 of the stator assembly 344. In an embodiment, opposing vanes may define a diameter d of about 30-35 mm, e.g., 34 mm, for securing the stator assembly 344 in position. However, other suitable sizes are possible, e.g., depending on the size of the stator assembly.

In addition, the free end of the outer portion 339 of each vane 332 is adapted to engage the shield 360 so that it can support and maintain the shield 360 in an operative position.

3.3 Shields

The first or upper shield 360 includes an inner annular flange 367 and an outer annular flange 369. The inner annular flange 367 is structured to engage the upper end of the tube 338 of the stator component 330, e.g., with a friction fit, and the outer annular flange 369 is structured to engage the outer portion 339 of the vanes 332, e.g., with a friction fit.

The second or lower shield 370 is supported and maintained by the second housing part 324 in an operative position. The hub 374 at the central portion of the shield 370 is shaped to direct the air flow down towards the outlet 328.

3.4 Housing

In the illustrated embodiment, the second housing part 324 of the housing 320 includes a plurality of stator vanes 325, e.g., between 2 and 100 (e.g., about 5-15)stator vanes, to direct airflow towards the outlet 328. As illustrated, the stator vanes 325 support the shield 370 within the second housing part 324 adjacent the outlet 328. Also, at least one of the stator vanes 325 includes a projection 327 adapted to extend through an opening 377 provided in the shield 370 to align and secure the shield 370 in position.

4. Support System for Blower

Each of the blowers 10, 210, 310 described above may be supported within an outer casing or chassis (e.g., forming a portion of a NIVV device such as a PAP device or flow generator). In an embodiment, each blower may be supported within the outer casing by a support system that is structured to provide support and provide a seal between the inlet and the outlet sides of the blower.

Figure 5:
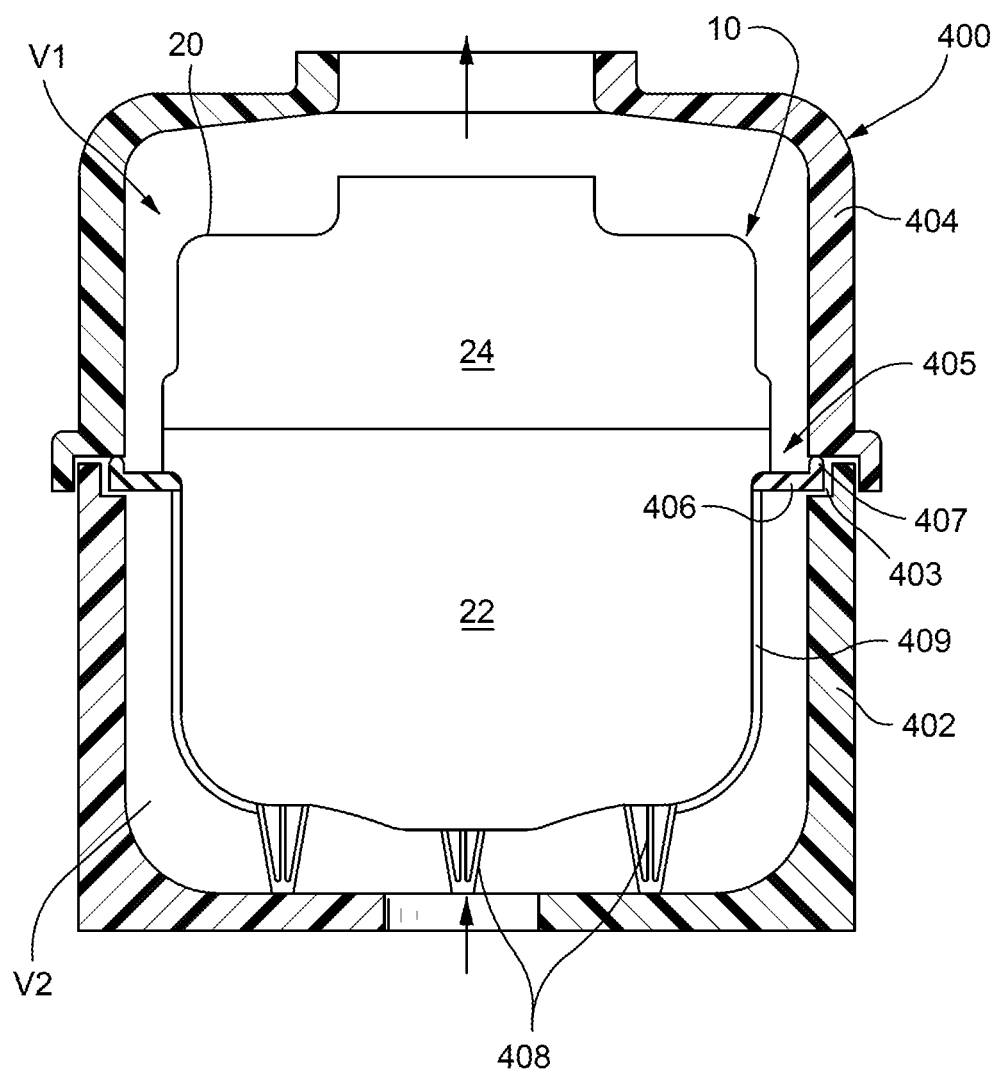
FIG. 5 is a cross-sectional view of a support system for a blower according to an embodiment of the present invention.

In an embodiment, as shown in FIG. 5, the outer casing 400 includes a base 402 and a cover 404 provided to the base 402. The support system 405 includes a side 406 support and a bottom support 408 to support the blower (e.g., blower 10).

As illustrated, the side support 406 is in the form of an annular ring (e.g., made of Silicone or TPE) that is provided to the blower housing (e.g., housing 20) and includes an end portion 407 adapted to engage within a respective slot 403 defined between the base 402 and cover 404. The bottom support 408 is in the form of multiple flexible feet or flexible pegs, e.g., 3 feet, that are adapted to engage the base wall of base 402. The annular ring 406 (also referred to as a divider seal or a soft girdle/seal) suspends/supports the blower 10 in the chassis and divides or seals the inlet side of the blower from the outlet side of the blower (i.e., divide or separate low and high pressure sides), e.g., to avoid the need for a connection tube that directs flow towards the outlet of the outer casing 400. The feet 408 may act as a backup seal between the inlet and outlet sides of the blower or a backup support for the blower, e.g., in case the ring 406 creeps in old age.

As illustrated, a relatively small outlet muffler volume V1 is provided on the outlet side of the blower and a relatively small inlet muffler volume is provided on the inlet side of the blower V2.

In an embodiment, the annular ring 406 and feet 408 may be overmolded onto the outside of the first housing part 22 of the blower 10 (i.e., the first stage cover of the blower). As illustrated, an overmolded feeder 409 may interconnect the overmolded ring 406 with each of the overmolded feet 408. For example, the first housing part 22 (along with the second housing part 24) may be constructed of a relatively rigid plastic material, e.g., polycarbonate (PC) or acrylonitrile butadiene styrene (ABS), and the overmolded ring 406, feet 408, and feeders 409 may be constructed of an elastomeric material, e.g., Versollan™ Alternative, the ring, feet, and/or feeders may be separate molded pieces that are attached in an operative position.

The support system 405 provides an arrangement that avoids the need for inlet and outlet seals adjacent the inlet and outlet of the blower. In addition, the support system 405 is constructed of an elastomeric material that isolates (e.g., vibration isolated) and/or serves as a suspension between the blower 10 and the outer casing 400, e.g., without using springs. In an embodiment, additional supports (e.g., feet or pegs) may be provided to the top and/or sides of the blower so that the outer casing and the blower supported therein may be oriented in any direction, e.g., casing may be positioned on its side rather than vertically.

5. Sealing Arrangement for Blower Housing

Each of the blowers 10, 210, 310 described above may include a sealing arrangement between the housing parts of the housing, e.g., to prevent leak or loss of pressure.

Figures 2, 6:
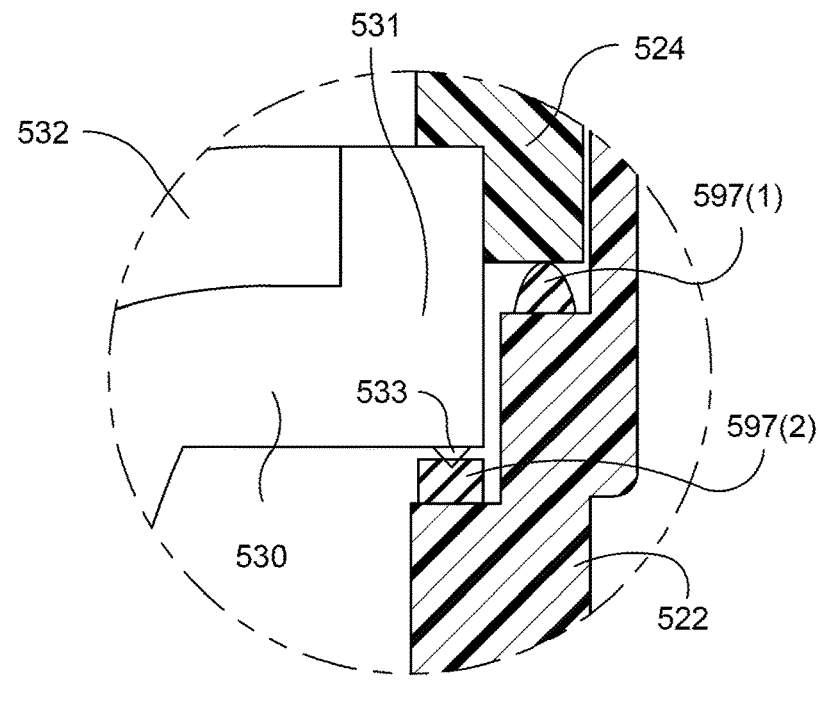
Figures 1, 6:
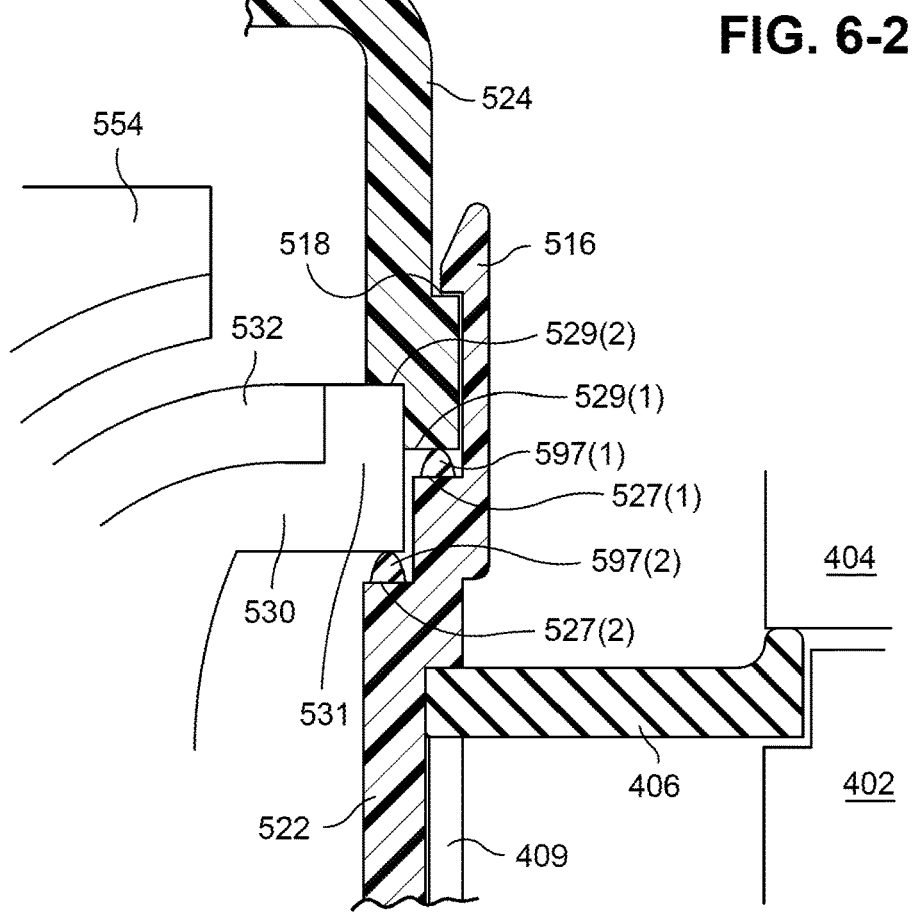

In an embodiment, as shown in FIG. 6-1, the end portion of the first housing part 522 of the blower (i.e., the first stage cover of the blower) includes a stepped configuration with first and second steps 527(1), 527(2). Each of the steps 527(1), 527(2) is provided with a sealing structure, i.e., first and second seals 597(1), 597(2) respectively. In an embodiment, the seals 597(1), 597(2) may be overmolded with the first housing part 522 in a manner as described above, e.g., elastomeric seals 597(1), 597(2) overmolded to relatively rigid plastic first housing part 522.

The end portion of the second housing part 524 of the blower includes a similar stepped configuration as the first housing part 522, e.g., first and second steps 529(1), 529(2).

As illustrated, when the first and second housing parts 522, 524 are coupled to one another, the first seal 597(1) of the first housing part 522 engages the first step 529(1) of the second housing part 524 to provide a seal between housing parts 522, 524. Also, the second step 527(2) of the first housing part 522 and the second step 529(2) of the second housing part 524 cooperate to define a slot adapted to receive and support the edge 531 of stator component 530 including stator vanes 532 (e.g., similar to stator component 30). The second seal 597(2) provides a seal between the stator component 530 and the housing parts 522, 524.

In addition, multiple snap-fit members 516, e.g., 3 snap-fit members, are provided to the end portion of the first housing part 522 that are adapted to engage a respective shoulder 518 provided to the second housing part 524 with a snap-fit. The snap-fit members 516 secure the first and second housing parts 522, 524 to one another and maintain the seal. However, it should be appreciated that the first and second housing parts may be secured to one another in other suitable manners, e.g., welding, adhesive (e.g., gluing), heat staking, fasteners (e.g., screws), etc.

FIG. 6-1 also illustrates an overmolded ring 406 and feeder 409 provided to the first housing part 522, and the ring 406 engaged within the slot between the base 402 and cover 404 of an outer casing as described above. In addition, FIG. 6-1 illustrates impeller 554 between stator component 530 and the outlet of the blower.

In an alternative embodiment, as shown in FIG. 6-2, the edge 531 of the stator component 530 may include a relatively rigid protrusion 533 (e.g., v-shaped protrusion) adapted to engage the second seal 597(2), e.g., to improve grip and sealing. Also, the second seal 597(2) may have a more block-like configuration, rather than a bead-like configuration as shown in FIG. 6-1.

6. Alternative Blower Embodiment

FIGS. 7-1 to 7-13 illustrate a blower 610 according to another embodiment of the present invention. Similar to the blowers 10, 210, 310 described above, the blower 610 includes two stages with one impeller 650 positioned on one side of the motor 640 and one impeller 652 positioned on the other side of the motor 640. Also, the blower 610 has axial symmetry with both the inlet 626 and outlet 628 aligned with an axis 615 of the blower 610.

6.1 General Description

A stationary portion of the blower 610 includes a housing 620 with first and second housing parts 622, 624, a stator component 630, and first and second shields 660, 670. A rotating portion of the blower 610 includes a rotatable shaft or rotor 680 adapted to be driven by motor 640 and first and second impellers 650, 652 (e.g., mixed flow) provided to end portions of the shaft 680. The motor 640 includes a magnet 642 provided to shaft 680 and a stator assembly 644 to cause spinning movement of the shaft 680 via the magnet 642.

The stator assembly 644 includes windings 646 and a stator or stator lamination stack 648 (e.g., slotless or toothless) provided to the windings 646. In an embodiment, the resistance of the windings 646 and/or current draw (e.g., at start-up) may be monitored to determine temperature, which may be used to indicate faults in the motor (e.g., bearing fault detection, bearing end of life failure or rubbing condition, software fault in the electronic drive systems). For example, after the motor has stopped but still remains warm, the resistance of the windings may be measured (e.g., via a circuit in the blower). It is noted that resistance of the windings changes with temperature in a known way. If the resistance was such that it implied a much hotter than usual temperature, the device would go into a fault mode, e.g., and prompt the user to have the blower serviced. Several blower faults tend to lead to unusually high temperatures, e.g., bearing end of life failures or software faults in electronic drive systems.

The inlet 626 is provided by the first housing part 622 (also referred to as a first stage cover) at one end and the outlet 628 is provided by the second housing part 624 (also referred to as a final stage cover) at the other end.

6.2 Stator Component

As best shown in FIGS. 7-7 to 7-10, the stator component 630 includes an annular base portion 634, a shield portion 636, a tube or bearing tube 638 extending from the shield portion 636, and a plurality of spaced apart side walls 632 extending between the base portion 634 and the shield portion 636. As illustrated, the stator component 630 forms a cylindrical "cage" and the spaced apart side walls 632 define openings 633 into the "cage". The stator component 630 may be integrally formed (e.g., injection molded) as a one-piece structure. However, the stator component 630 may be constructed in other suitable manners and/or may be made in separate parts.

Figures 1, 7:
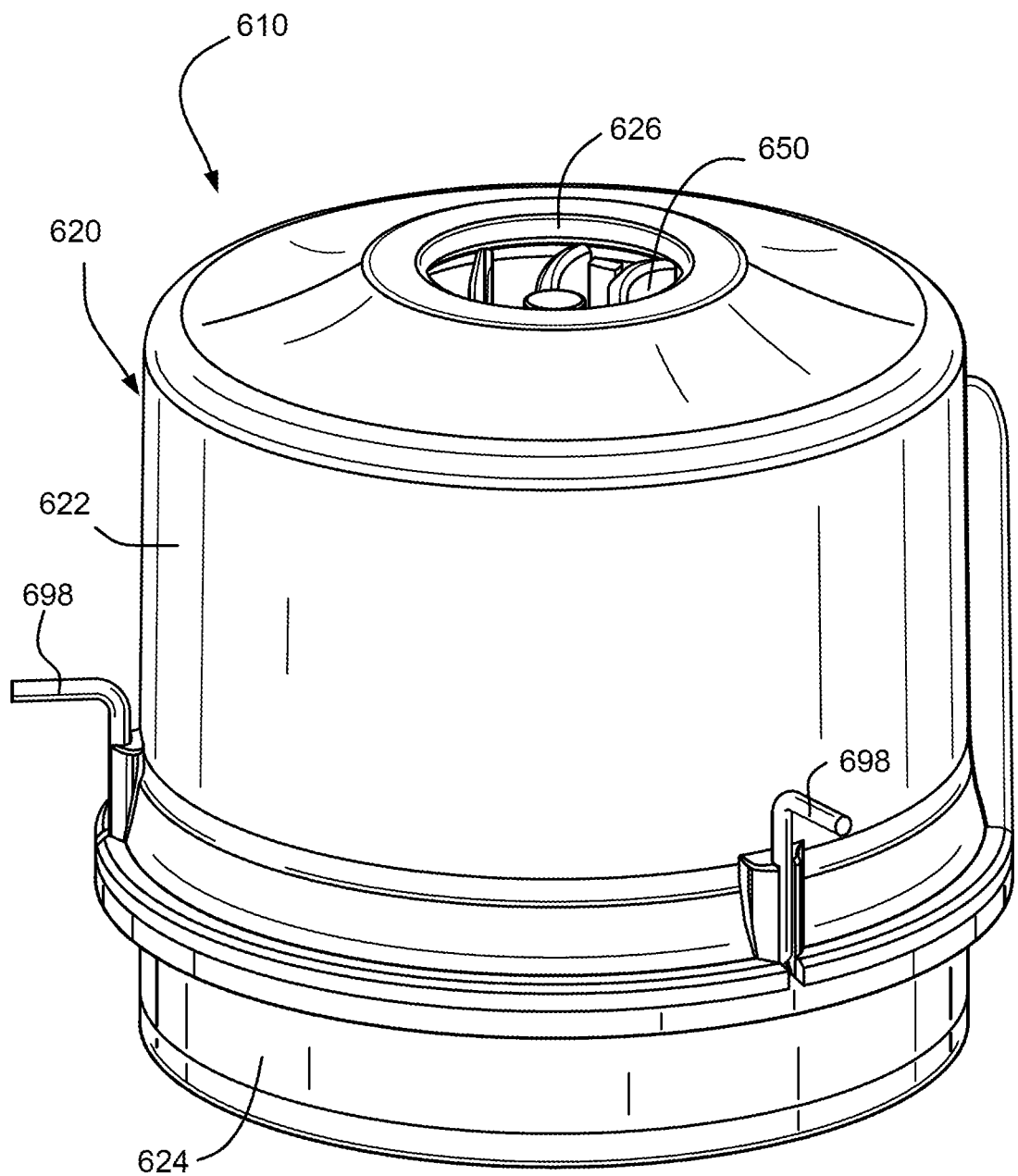
Figures 2, 7:
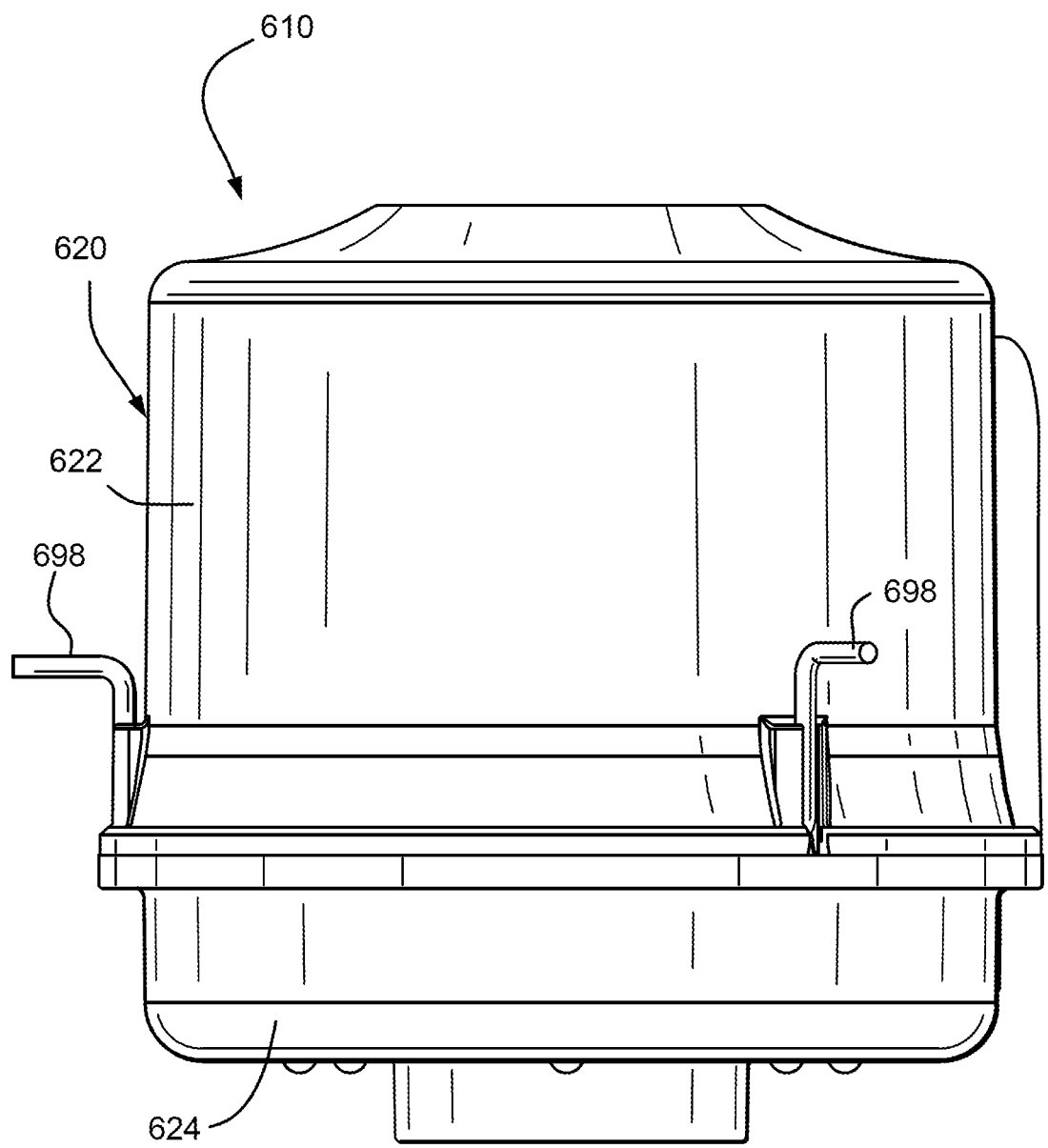
Figures 3, 7:
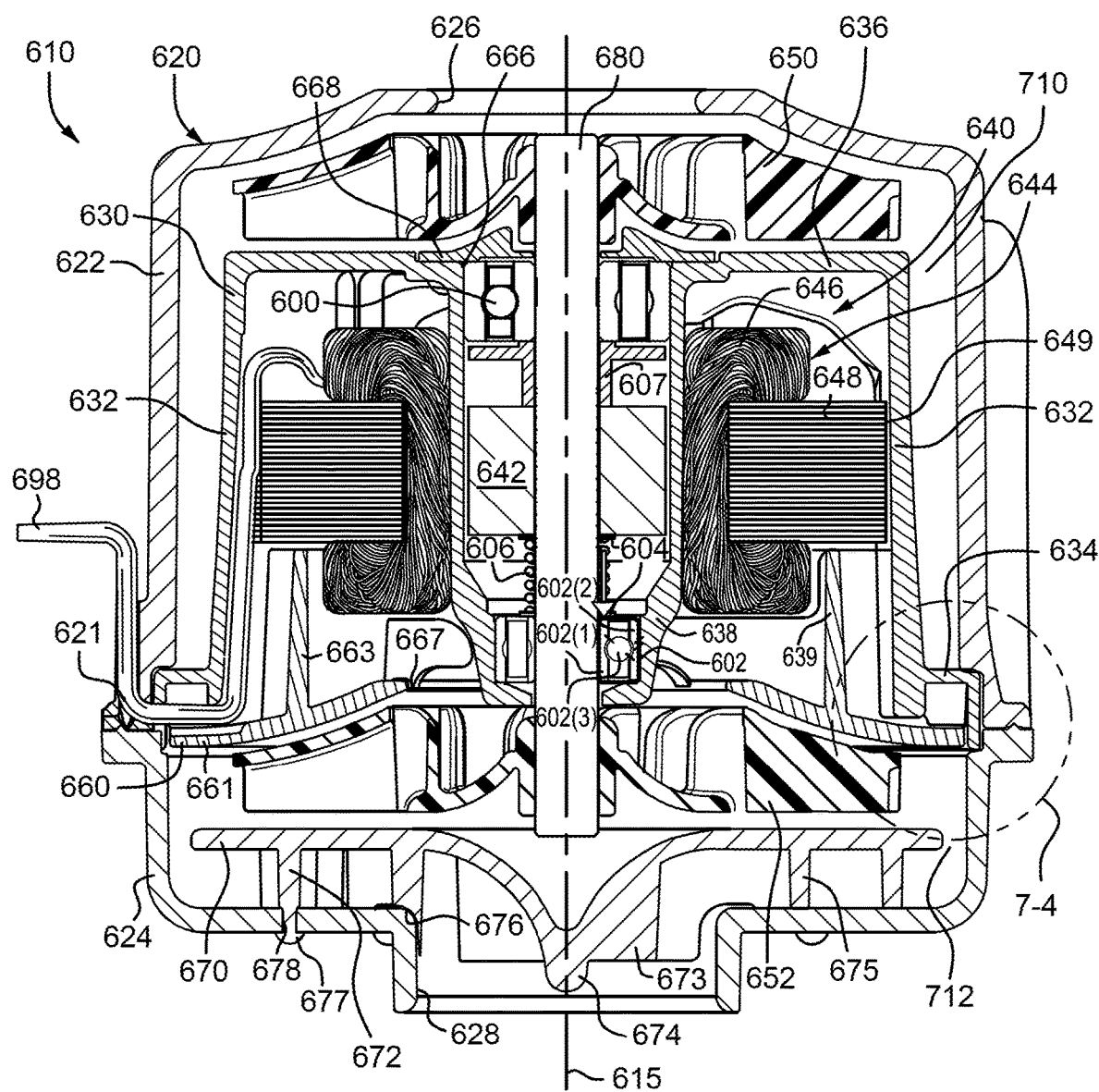
Figures 4, 7:
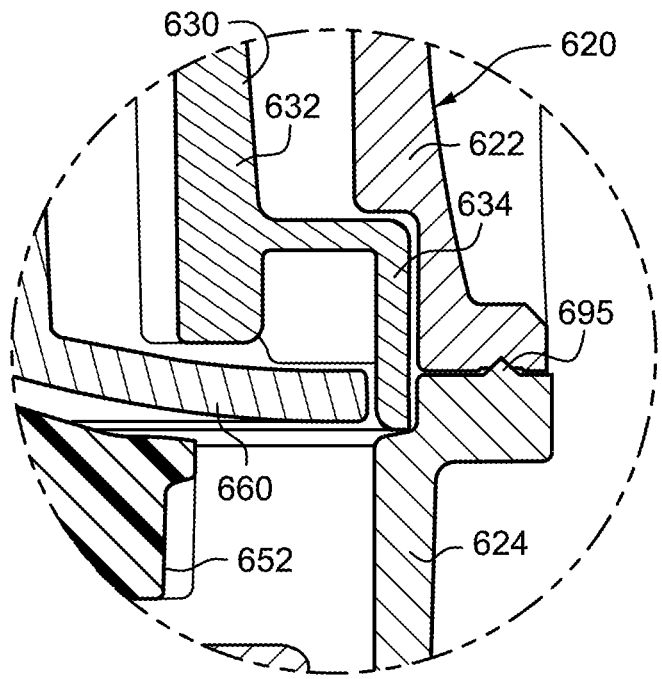

As best shown in FIGS. 7-3 to 7-5, the base portion 634 is sandwiched between the first and second housing parts 622, 624 to support the stator component 630 within the housing 620. In addition, the second housing part 624 may include a protrusion 695 (e.g., v-shaped protrusion as best shown in FIG. 7-4) adapted to engage the first housing part 622, e.g., to improve grip and sealing.

Figures 4B, 7:
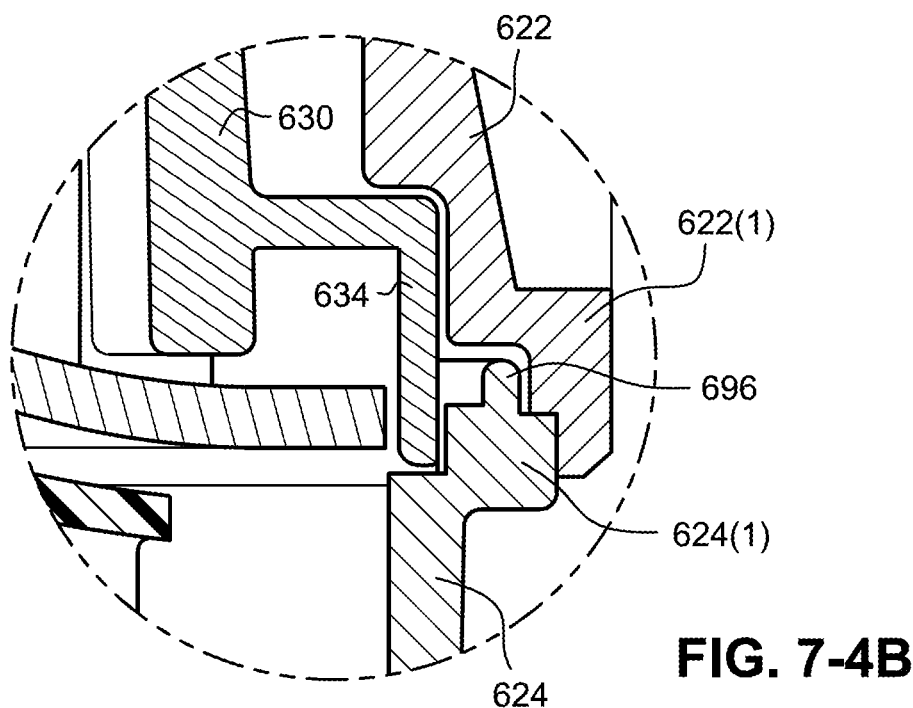
Figures 5, 7:
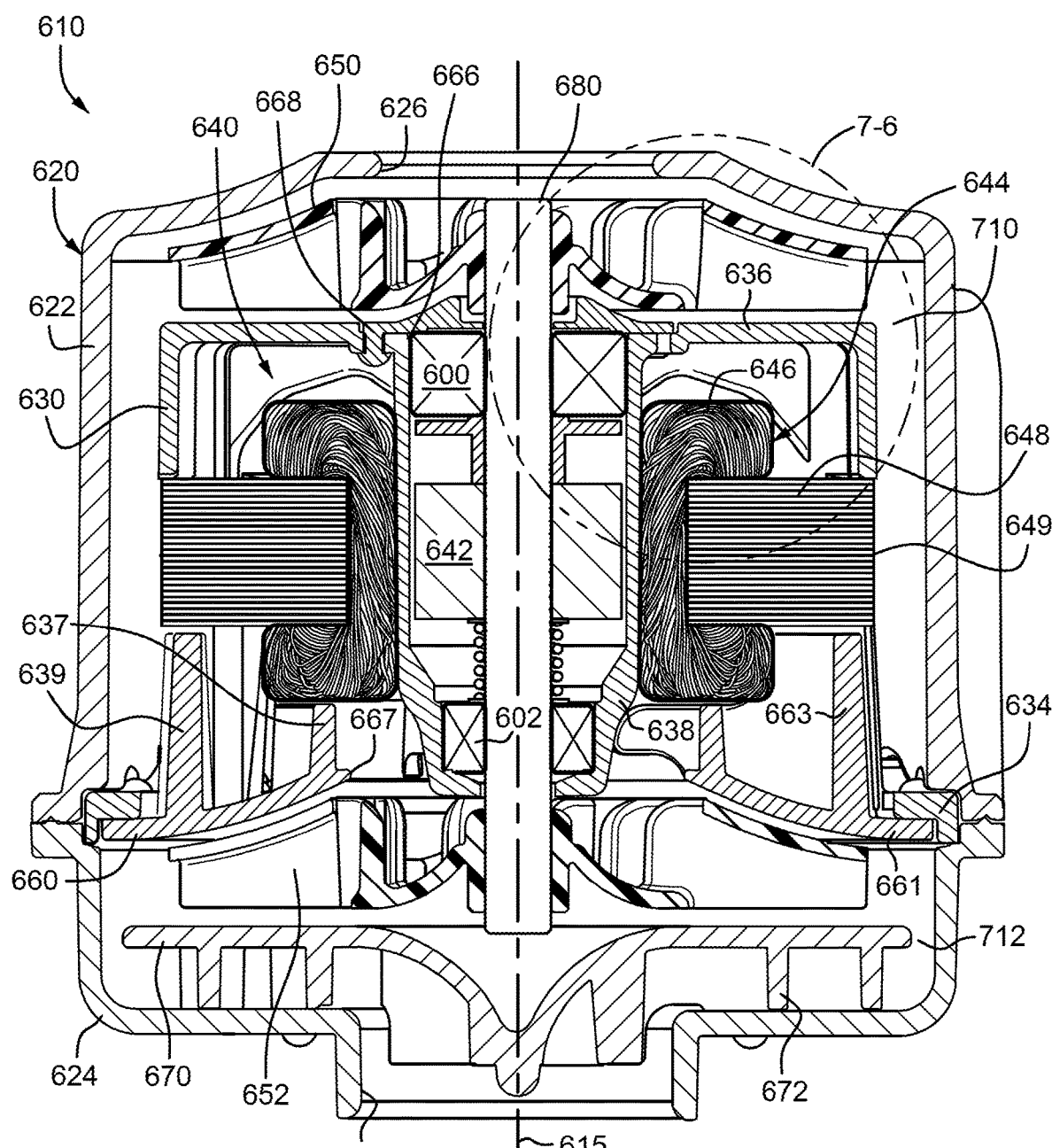
Figures 6, 7:
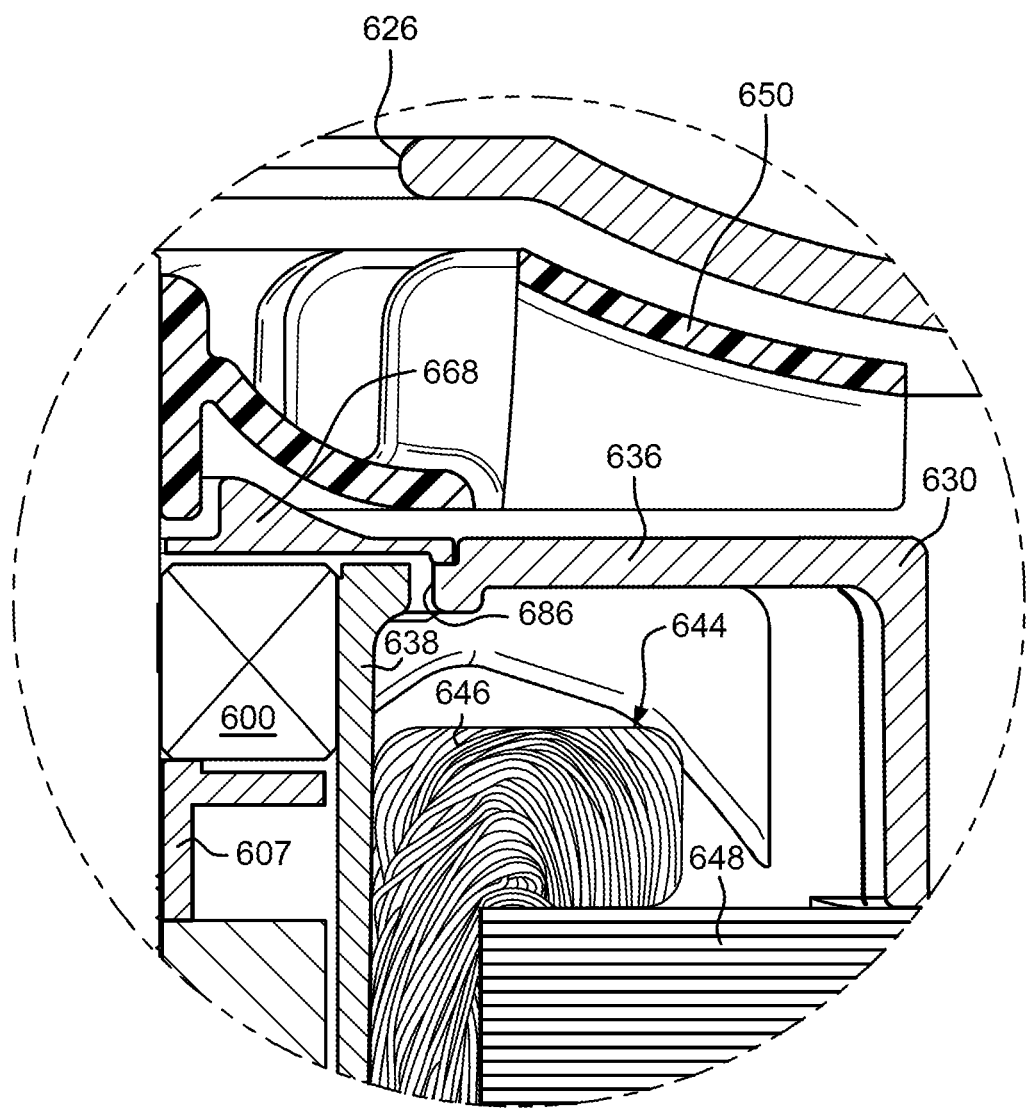
Figure 7:
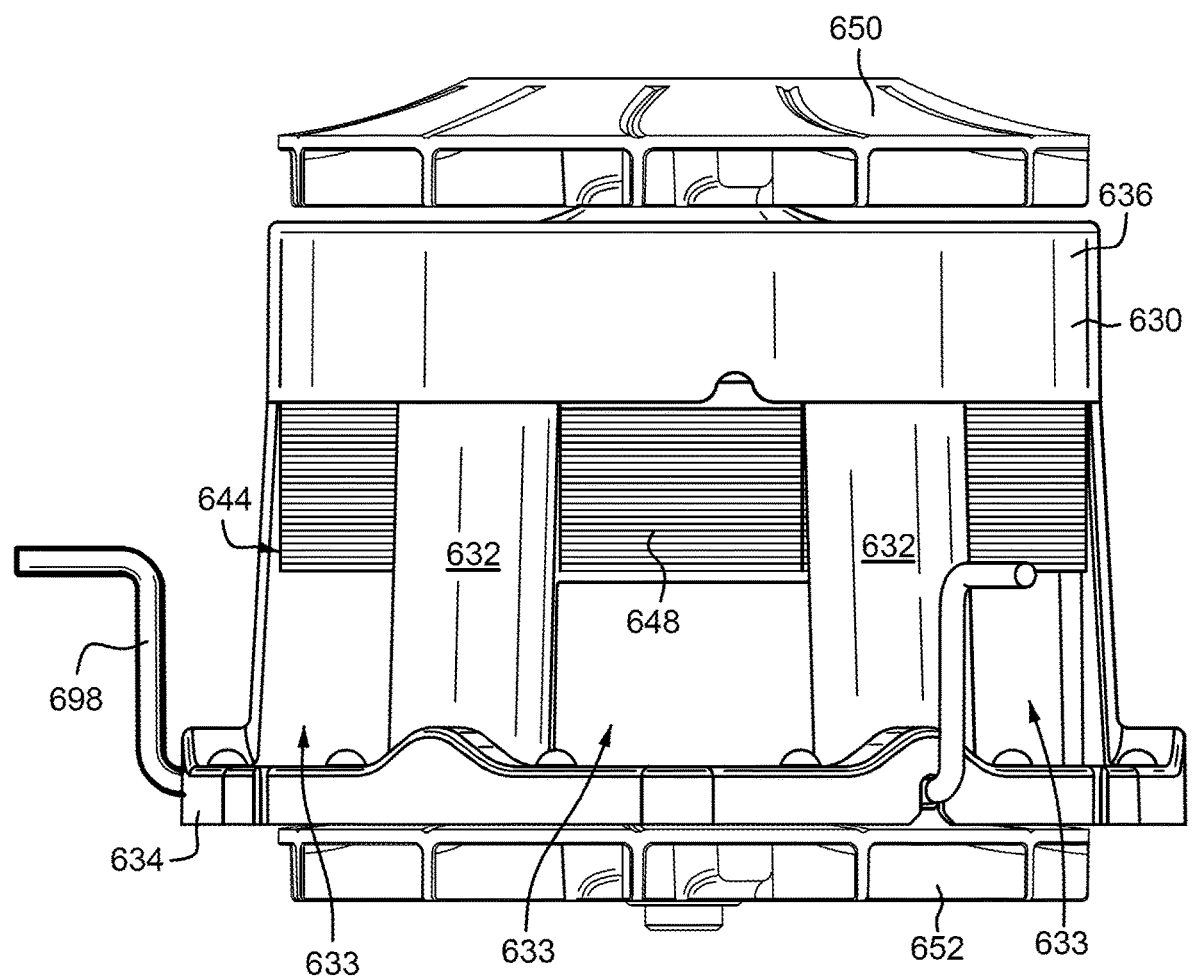

In an alternative embodiment, as shown in FIG. 7-4B, the first housing part 622 may include a connecting portion 622(1) structured to overlap and/or overhang a connecting portion 624(1) of the second housing part 624. Similar to the above embodiment, the base portion 634 of the stator component 630 is sandwiched between the first and second housing parts 622, 624. In addition, the second housing part 624 may include a protrusion 696 for sealing against the first housing part 622.

The outer edge of the shield portion 636 substantially aligns with or extends radially beyond the outer edge of the impeller 650. The shield portion 636 provides a narrow annular gap 710 between its outer edge and the side wall of the housing part 622, which is sufficient to direct gas into the stator component 630. The shield portion 636 includes an opening 666 that allows access to the interior of the tube 638.

6.2.1 Bearing Alignment and Retention

Similar to the above embodiments, the tube 638 is structured to retain and align bearings 600, 602 (e.g., of mixed bearing sizes) that rotatably support the shaft 680. In addition, the tube 638 is sufficiently "magnetically transparent", which allows the stator assembly 644 to act on the magnet 642 positioned within the tube 638 without significant loss of flux density and/or increased heat, if any.

Also, the tube 638 may be constructed of an acoustically damped material to damp vibrations caused by rotor operation, e.g., polypropylene, nylon (reinforced), liquid crystal polymer (LCP) with ceramic loading (conduct heat), polyphenylene sulfide (PPS) with graphite fill, polyetheretherketone (PEEK). If ball bearings are utilized, the number of balls within the bearings may be optimized to minimize vibrations.

A cap portion 668 is provided to the shield portion 636 along the opening 666. The cap portion 668 provides a stop for the bearing 600 and hence retains the shaft 680 within the tube 638. In addition, the cap portion 668 may act as a spacer for the impeller 650.

Washers 604 and a spring or biasing element 606 may be provided between the bearing 602 and the rotor magnet 642 and a spacer 607 may be provided between the bearing 600 and the rotor magnet 642, e.g., to maintain alignment/spacing of the rotor magnet 642 with the stator assembly 644, act as wear stop, and/or provide a pre-load. Also, the spacer 607 (e.g., constructed of metallic ferrite) adjacent the bearing 600 acts as a magnetic shunt or flux shield to direct magnetic field towards the windings 646 and away from the bearing 600, e.g., to avoid heating bearing. It should be appreciated that such a spacer or shield may also be provided adjacent the bearing 602. The flux shield may be an optional component, but may increase bearing/lube life due to reduced eddy current losses in the bearing outer races and balls.

As shown in FIG. 7-3, the spring 606 provides an inner race pre-load (IRP), e.g., about 1.25 lb spring load, on the bearing 602. Specifically, the bearing 602 includes an inner race 602(1), an outer race 602(2), and ball bearings 602(3) provided between the inner and outer races (e.g., there may be a clearance between the ball bearings and the races). The inner and outer races 602(1), 602(2) provide surfaces upon which the ball bearings 602(3) run. Also, the bearing may include a spacer element between the inner and outer races to maintain spacing between the ball bearings (e.g., cylinder with openings to receive respective ball bearings). In the illustrated embodiment, the spring 606 is constructed and arranged to engage the inner race 602(1) of the bearing 602 to provide a spring load to the bearing, which brings the ball bearings into contact with the races (i.e., load transmitted from the inner race to the ball bearings, and from the ball bearings to the outer race).

In an alternative embodiment, the spring may be constructed and arranged to provide an outer race pre-load (ORP) on the bearing, e.g., see FIGS. 8 and 9-1 to 9-2 described below.

6.2.2 Alternative Airflow Path

Figures 7, 8:
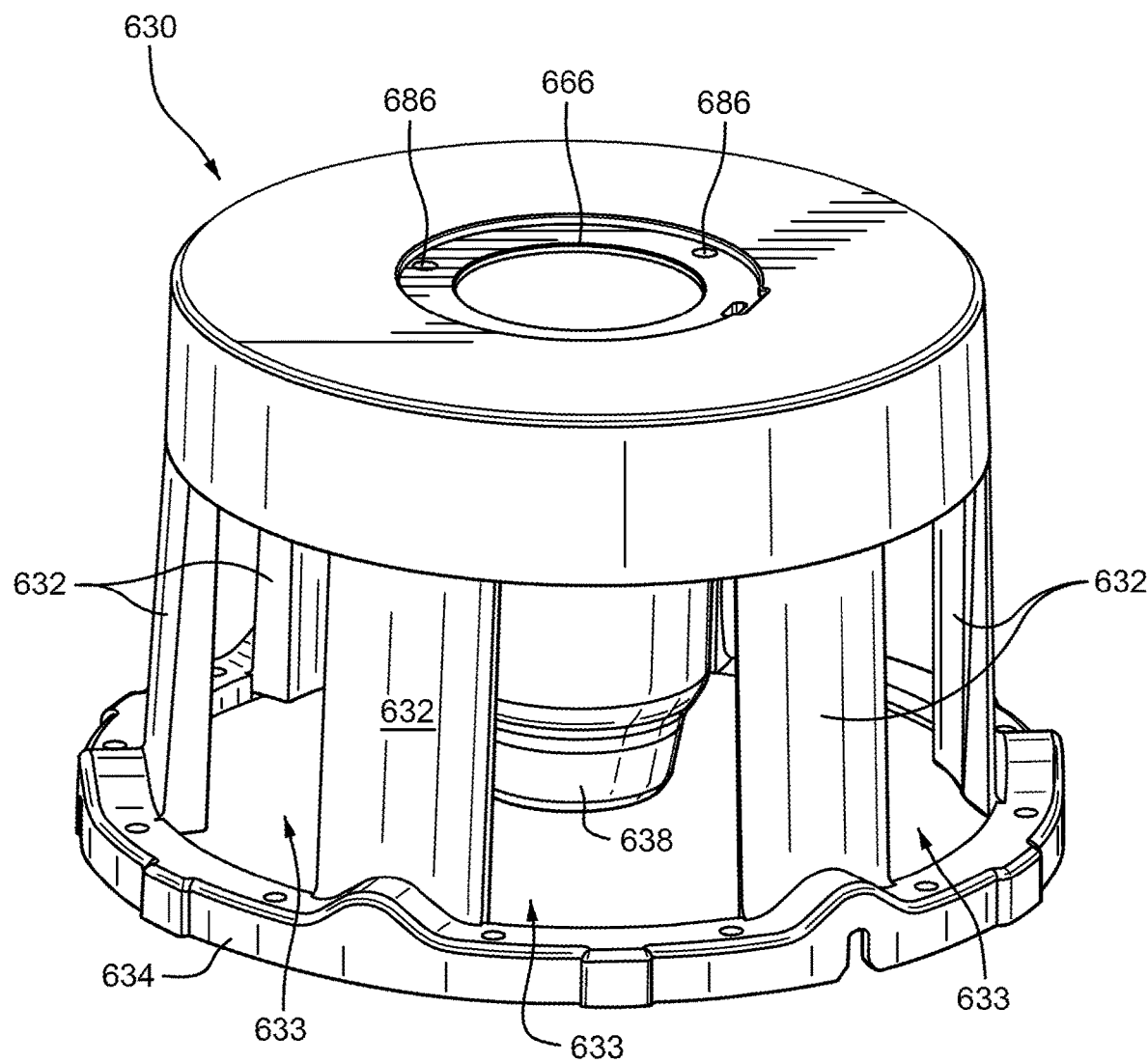

Similar to the embodiment described above, the shield portion 636 and cap portion 668 cooperate to provide by-pass passages or conduits 686 (as shown in FIGS. 7-6 and 7-8) to provide pressure balance across the bearings 600, 602. Specifically, the by-pass passages 686 provide a short circuit of pressure around the tube 638 and hence the bearings 600, 602.

In an embodiment, a tight tolerance (i.e., a small gap) is provided between the inner diameter of the cap portion 668 and the shaft 680 which increases the impedance between the cap portion 668 and the shaft 680. Hence, air can flow with less resistance through the by-pass passage or bleed hole 686 (e.g., tight tolerance may also apply to the by-pass arrangement shown in FIG. 1-1).

Without a by-pass, air may flow through the bearings, upwards from the high pressure side to the low pressure side. The by-pass passage connects the high pressure zone to a point above the top bearing. This means high pressure exists more or less equally across the pair of bearings. Therefore, there is little flow through the bearings, and the grease neither dries out nor gets displaced, thereby improving bearing longevity.

6.2.3 Stator Assembly Alignment and Retention

The stator assembly 644 is provided along the exterior surface of the tube 638. In addition, the stator component 630 and first shield 660 cooperate to support and maintain the stator assembly 644 in an operative position, as described in greater detail below.

6.3 First Shield

As best shown in FIGS. 7-11 to 7-12, the first shield 660 includes a base 661 and a plurality of stator vanes 663 provided to the base 661. The first shield 660 is attached to the stator component 630, e.g., by engaging pins 665 on the first shield 660 with respective openings 635 provided in the base portion 634 of the stator component 630 (e.g., pins heat staked into position). However, the first shield 660 may be attached to the stator component 630 in other suitable manners.

The plurality of stator vanes 663, e.g., between 2 and 100 stator vanes, are structured to direct airflow towards an orifice 667 in the base 661. In the illustrated embodiment, the stator component 630 has six stator vanes 663. Each vane 663 is substantially identical and has a generally spiral shape. In addition, each vane 663 includes an inner portion 637 (adjacent the orifice 667) and an outer portion 639. As best shown in FIG. 7-11, the inner portion 637 is recessed (e.g., reduced in height) with respect to the outer portion 639.

As best shown in FIGS. 7-3 and 7-5, the windings 646 of the stator assembly 644 are engaged or supported by the recessed, inner portion 637 of the stator vanes 663, and the stack 648 of the stator assembly 644 is engaged or supported by the outer portion 639 of the stator vanes 663.

Figures 7, 8, 9:
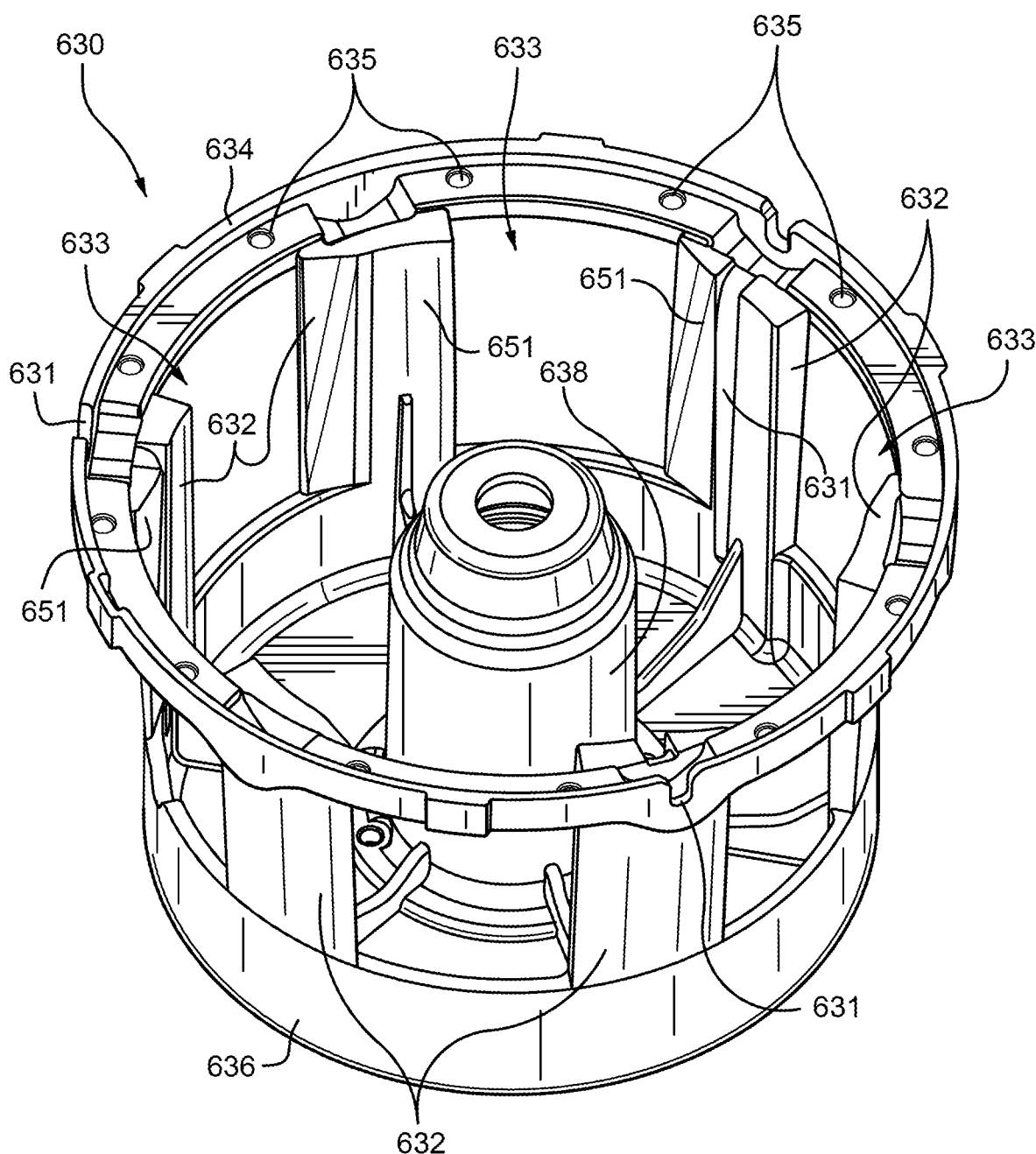

In addition, the exterior surface 649 of the stack 648 (e.g., see FIGS. 7-3 and 7-5) includes a toothed configuration that is adapted to engage or interlock with spaced-apart teeth 651 provided by interior surfaces of the spaced apart side walls 632 (e.g., see FIG. 7-9). Remaining portions of the toothed configuration of the stack 648 at least partially protrude through the openings 633 in the stator component 630, e.g., flush with exterior surfaces of the side walls 632 (see FIGS. 7-5 and 7-7). Thus, the stator component 630 and first shield 660 cooperate to retain or secure the stator assembly 644 in an operative position.

As shown in FIGS. 7-1 to 7-3 and 7-7, wires 698 (e.g., three wires for a three phase motor) extend from the windings 646 to outside the housing 620 to conduct current from an external source to the windings 646. As illustrated, slots 631 are provided through the stator component 630 (see FIG. 7-9) and slots 621 are provided through the housing 620 (see FIG. 7-3) to accommodate passage of respective wires 698 from the windings 646 to outside the housing 620.

In the illustrated embodiment, the stack 648 and windings 646 are exposed to the flow of gas, e.g., via the openings 633 in the stator component 630, as shown in FIGS. 7-3, 7-5, and 7-7. This arrangement allows forced-convection cooling of the stack 648/windings 646 as gas flows through the stator component 630 in use. In addition, this arrangement may assist in heating the patient air.

6.4 Second Shield

As shown in FIG. 7-13, the second shield 670 includes a plurality of stator vanes 672, e.g., between 2 and 100 stator vanes, to direct airflow towards the outlet 628. In the illustrated embodiment, the shield 670 has 7 stator vanes. Each vane 672 is substantially identical and has a generally spiral shape. In addition, each vane 672 includes an inner portion 673 (adjacent the hub 674) and an outer portion 675. As best shown in FIGS. 7-3 and 7-5, the outer portion 675 is recessed (e.g., reduced in height) with respect to the inner portion 673, and a contoured edge 676 extends between the inner and outer portions 673, 675.

In the illustrated embodiment, the stator vanes 672 support the shield 670 within the second housing part 624 adjacent the outlet 628. As illustrated, the contoured edge 676 of the shield 670 engages the edge of the outlet 628 to align the shield 670 with the outlet 628 (see FIG. 7-3). The hub 674 and inner portion 673 of the vanes 672 extend at least partially through the outlet 628 and the outer portion 675 of the vanes 672 engage the lower wall of the second housing part 624, as best shown in FIG. 7-3. The hub 674 at the central portion of the shield 670 is shaped to direct the air flow down towards the outlet 628.

In addition, the second shield 670 includes pins 677 that are adapted to engage with respective openings 678 provided in lower wall of the second housing part 624, e.g., pins heat staked into position, as shown in FIG. 7-3. However, the second shield 670 may be attached to the second housing part 624 in other suitable manners.

The second shield 670 (also referred to as a final stage disc) includes a disc or shield to cover the stator vanes 672 in order to keep any discontinuities away from the blades of the impeller 652. However, other structure may be provided to keep any discontinuities away from the impeller blades. For example, the stator vanes 672 may be integrated into the second housing part 624, and the impeller 652 may include a lower shroud to act as a rotating shroud or shield between the impeller blades and stator vanes 672.

6.5 Fluid Flow Path

In the first stage, air enters the blower 610 at the inlet 626 and passes into the first impeller 650 where it is accelerated tangentially and directed radially outward. It is noted that suction is developed at the inlet to draw air into the blower. Air then flows in a spiral manner with a large tangential velocity component and also an axial component passing through the gap 710 defined by the outer edge of the shield portion 636 and the side wall of housing part 622. Air then enters the stator component 630 via the openings 633 in the stator component 630, and flows into the stator vanes 663 of the first shield 660 where it is directed radially inwardly towards orifice 667, and thereafter onto the second stage.

In the second stage, air passes into the second impeller 652 where it is accelerated tangentially and directed radially outward. Air then flows in a spiral manner with a large tangential velocity component and also an axial component passing through the gap 712 defined by the outer edge of the second shield 670 and the side wall of housing part 624. Air then enters the stator vanes 672 formed in the shield 670 and is directed towards the outlet 628.

6.5.1 Alternative Structure to Direct Flow

In the above-described embodiments, the blowers include stator vanes to direct airflow towards a second stage and towards the outlet. Such stator vanes help to straighten the flow and remove the "swirl" caused by the impellers. In alternative embodiments, the stator vanes may be replaced with alternative structure to direct or straighten flow. For example, a grid, mesh (e.g., woven), honeycomb-like structure, and/or extrusion (e.g., helical) may be provided to direct flow in use.

Also, in an alternative embodiment, multiple tangential feeds may be provided to the axial outlet 628 to direct flow tangentially from the outlet.

7. Tube as a Mandrel

In an embodiment, the tube of the stator component may be used as a mandrel to help form the windings of the stator assembly. The tube may be structured and shaped to facilitate its use as a mandrel. For example, the cylindrical and tapered construction of the tube may facilitate its use as a mandrel. The shape may be polygonal, e.g., rectangle, triangle, square, pentagon, hexagon, etc. In addition, the tube may include one or more structural components, such as splines, to aid with separation of the windings from the mandrel.

8. Interstage Seal

FIG. 8 illustrates a blower according to another embodiment of the present invention. The blower is similar to blower 610 described above and indicated with similar reference numerals. In contrast, the first shield 660 (i.e., the interstage "de-swirl" vane) includes a lip region or flange 660(1) adapted to engage or seal against the second housing part 624. Specifically, the lip region 660(1) of the first shield 660 is structured to engage the base portion 634 of the stator component 630, and the lip region 660(1) and base portion 634 are supported and/or sandwiched between the first and second housing parts 622, 624 to support the first shield 660 and the stator component 630 within the housing 620. Moreover, the lip region/base portion arrangement is structured to provide an interstage seal to prevent air leakage from the second stage back into the first stage in use. In addition, the connecting portion 622(1) of the first housing part 622 is structured to overlap and/or overhang the connecting portion 624(1) of the second housing part 624.

However, an interstage seal may be provided in other suitable manners. For example, a gasket or gooey sealant may be used at the interfaces of the shield 660, stator component 630, and housing parts 622, 624. In another embodiment, one or more of the interface surfaces may be overmolded with a soft silicone or TPE.

9. Blower with Metal Bearing Support

FIGS. 9-1 to 9-2 illustrate a blower 810 according to another embodiment of the present invention. Similar to the blowers described above, the blower 810 includes two stages with one impeller 850 positioned on one side of the motor 840 and one impeller 852 positioned on the other side of the motor 840. Also, the blower 810 has axial symmetry with both the inlet 826 and outlet 828 aligned with an axis 815 of the blower 810.

In contrast to the blowers described above, the bearings 800, 802 that support shaft 880 are retained by a metal housing assembly (rather than a plastic tube), as described in greater detail below. It is noted that the metal housing assembly includes a "cage"-like adaptor that supports the metal housing assembly within the blower housing and allows gas to flow into the first shield and onto the second stage in a similar manner to the "cage" like stator component described above.

9.1 General Description

A stationary portion of the blower 810 includes a housing 820 with first and second housing parts 822, 824, a metal housing assembly 830, and first and second shields 860, 870. A rotating portion of the blower 810 includes a rotatable shaft or rotor 880 adapted to be driven by motor 840 and first and second impellers 850, 852 provided to end portions of the shaft 880. The motor 840 includes a magnet 842 provided to shaft 880 and a stator assembly 844 to cause spinning movement of the shaft 880 via the magnet 842.

9.2 Metal Housing Assembly

The housing assembly 830 is constructed of a metallic material and includes a main housing 832, an end bell 834, and an adaptor 836 (e.g., secured to one another by one or more fasteners 838). As illustrated, the main housing 832 provides a recess for supporting bearing 800 and the end bell 834 provides a recess for supporting bearing 802. The main housing and end bell are structured to support bearings of the same size. However, the main housing and end bell may be structured to support mixed bearing sizes.

The metal bearing support provided by the housing assembly 830 improves heat transfer from the bearings in use. Also, the main housing 832, end bell 834, and adaptor 836 (e.g., constructed of aluminum) may be machined bar stock. In an embodiment, the end bell and adaptor may be aluminum die cast pieces for high volume production.

As best shown in FIG. 9-2, the adaptor 836 forms a cylindrical "cage" that defines openings 833 into the cage.

9.3 Stator Assembly Alignment and Retention

The main housing 832 and end bell 834 cooperate to support and maintain the stator assembly 844 in an operative position.

9.4 Interstage Seal

Similar to the FIG. 8 embodiment described above, a lip region 860(1) of the first shield 860 is structured to engage the base 836(1) of the adaptor 836, and the lip region 860(1) and base 836(1) are supported and/or sandwiched between the first and second housing parts 822, 824 to support the first shield 860 and housing assembly 830 within the housing 820. In addition, the lip region/base arrangement is structured to provide an interstage seal to prevent air leakage from the second stage back into the first stage in use.

9.5 Outer Race Preload (ORP)

In the illustrated embodiment, a spacer or flux shield 804 is provided between each bearing 800, 802 and the rotor magnet 842. In addition, a spring or biasing element 806 is provided between the bearing 802 and the end cap 834.

The spring 806 (e.g., crest-to-crest spring) provides an outer race preload (ORP) (outer race preload also shown in FIG. 8) on the bearing 802 (instead of an inner race preload such as that shown in FIG. 7-3). Specifically, the spring 806 is constructed and arranged to engage the outer race 802(2) of the bearing 802 to provide a spring load to the bearing, which brings the ball bearings into contact with the races (i.e., load transmitted from the outer race 802(2) to the ball bearings 802(3), and from the ball bearings 802(3) to the inner race 802(1)).

In an embodiment, the ORP arrangement may reduce or eliminate corrosion of the second stage bearing 802 (e.g., at the inner race) over the life of the blower.

9.6 Fluid Flow Path

In the first stage, air enters the blower 810 at the inlet 826 and passes into the first impeller 850 where it is accelerated tangentially and directed radially outward. It is noted that suction is developed at the inlet to draw air into the blower. Air then flows in a spiral manner with a large tangential velocity component and also an axial component passing through the gap 910 defined by the outer edge of the housing assembly 830 and the side wall of housing part 822. Air then flows into the stator vanes 863 of the first shield 860 via the openings 833 in the adaptor 836 where it is directed radially inwardly onto the second stage.

In the second stage, air passes into the second impeller 852 where it is accelerated tangentially and directed radially outward. Air then flows in a spiral manner with a large tangential velocity component and also an axial component passing through the gap 912 defined by the outer edge of the second shield 870 and the side wall of housing part 824. Air then enters the stator vanes 872 formed in the shield 870 and is directed towards the outlet 828.

10. Closed Slot External Winding

Figures 7, 8, 9, 10:
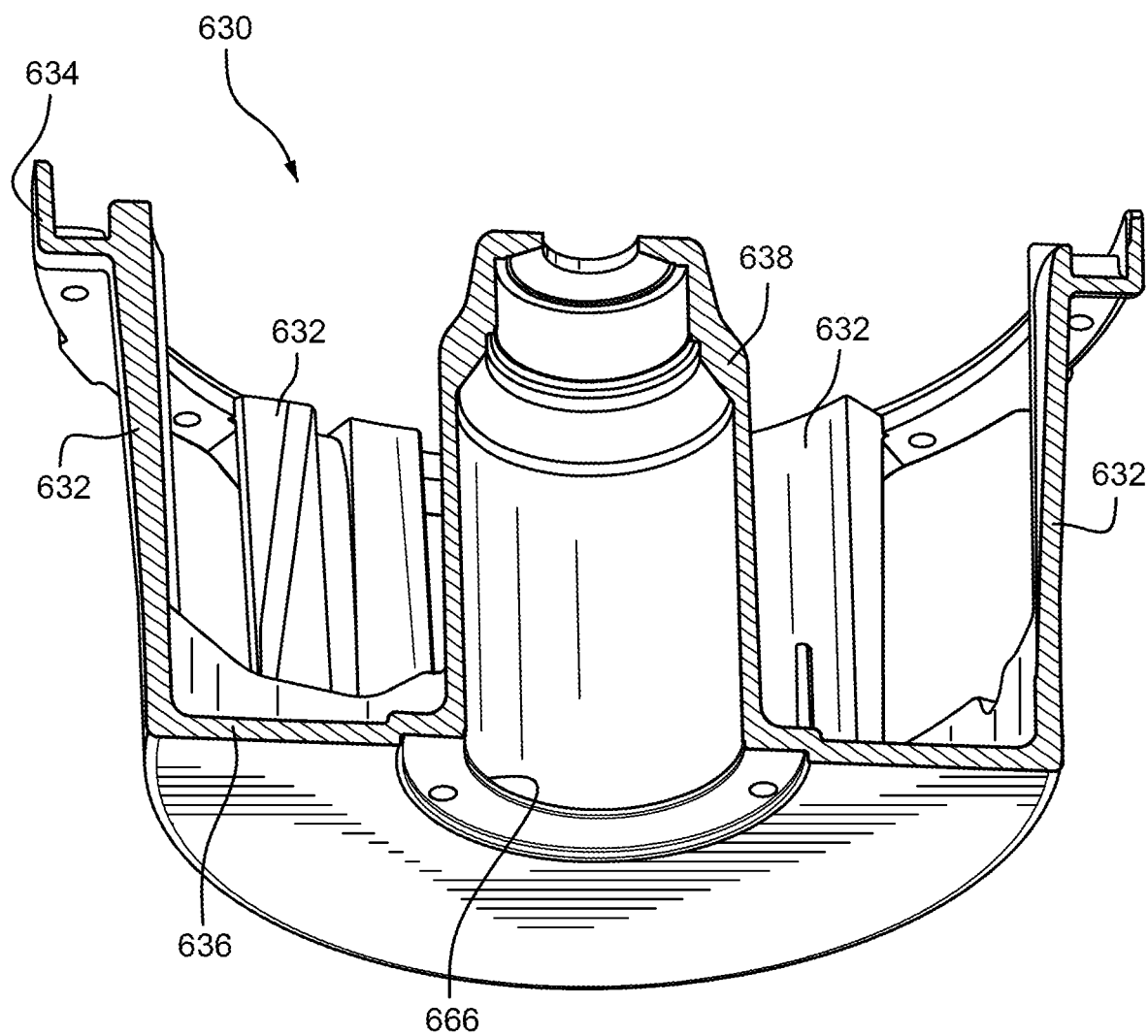

FIGS. 10-1 to 10-3 illustrate a stator 948 for a stator assembly according to an embodiment of the present invention. The stator 948 includes an outer portion 948(1) (FIG. 10-1) and an inner portion 948(2) (FIG. 10-2) structured to be received within the outer portion 948(1). FIG. 10-3 shows the stator 948 with the assembled outer and inner portions 948(1), 948(2).

The inner portion 948(2) has a plurality of stator teeth 949, e.g., six stator teeth, on which stator coils or windings are wound. The outer portion 948(1) is ring shaped and includes a plurality of recesses 950 along its inner circumference adapted to receive respective teeth of the inner portion 948(2). When assembled, the stator 948 provides a closed slot arrangement.

The outer circumference of the outer portion 948(1) includes a toothed configuration that is adapted to engage or interlock with the stator component (e.g. for use in blower 610 similar to the arrangement described above in relation to FIGS. 7-7 and 7-9). In addition, one or more slots 951 may be provided in the outer circumference of the outer portion 948(1) to accommodate passage of respective wires from the windings.

This "closed-slot" stator-core arrangement facilitates the insertion of magnet wire because magnet wire can be inserted from the outside via a generously wide slot opening. That opening becomes closed when the outer portion 948(1) is provided to the toothed inner portion 948(2). In its final assembled form, there is no opening of the slot, and as such, there is little magnetic detent (or magnetic cogging effect) produced by the interaction of the rotor's salient poles and the stator. It is a cost-effective, low cogging configuration.

Figures 7, 8, 9, 10, 11:
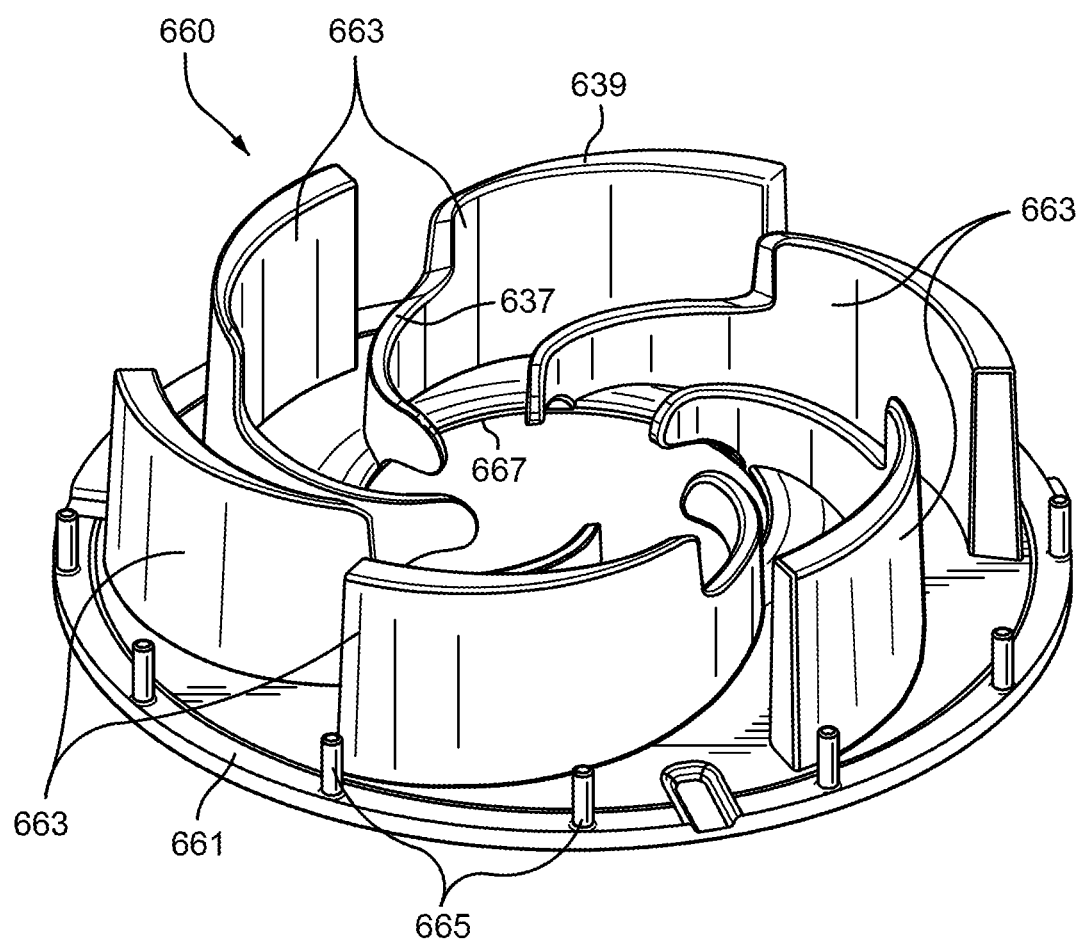

In the illustrated embodiment, each tooth 949 of the inner portion 948(2) has a generally T-shaped arrangement with substantially square edges. In an alternative embodiment, as shown in FIG. 11, the end portion of each tooth 949 (and corresponding recesses 950 in the outer portion 948(1)) may be more rounded.

In yet another embodiment, the stator assembly may include an ironless and slotless stator (i.e., using air as the flux return path, rather than using iron to concentrate the flux).

11. Blower with Slotted Stator

Figures 7, 8, 9, 10, 11, 12:
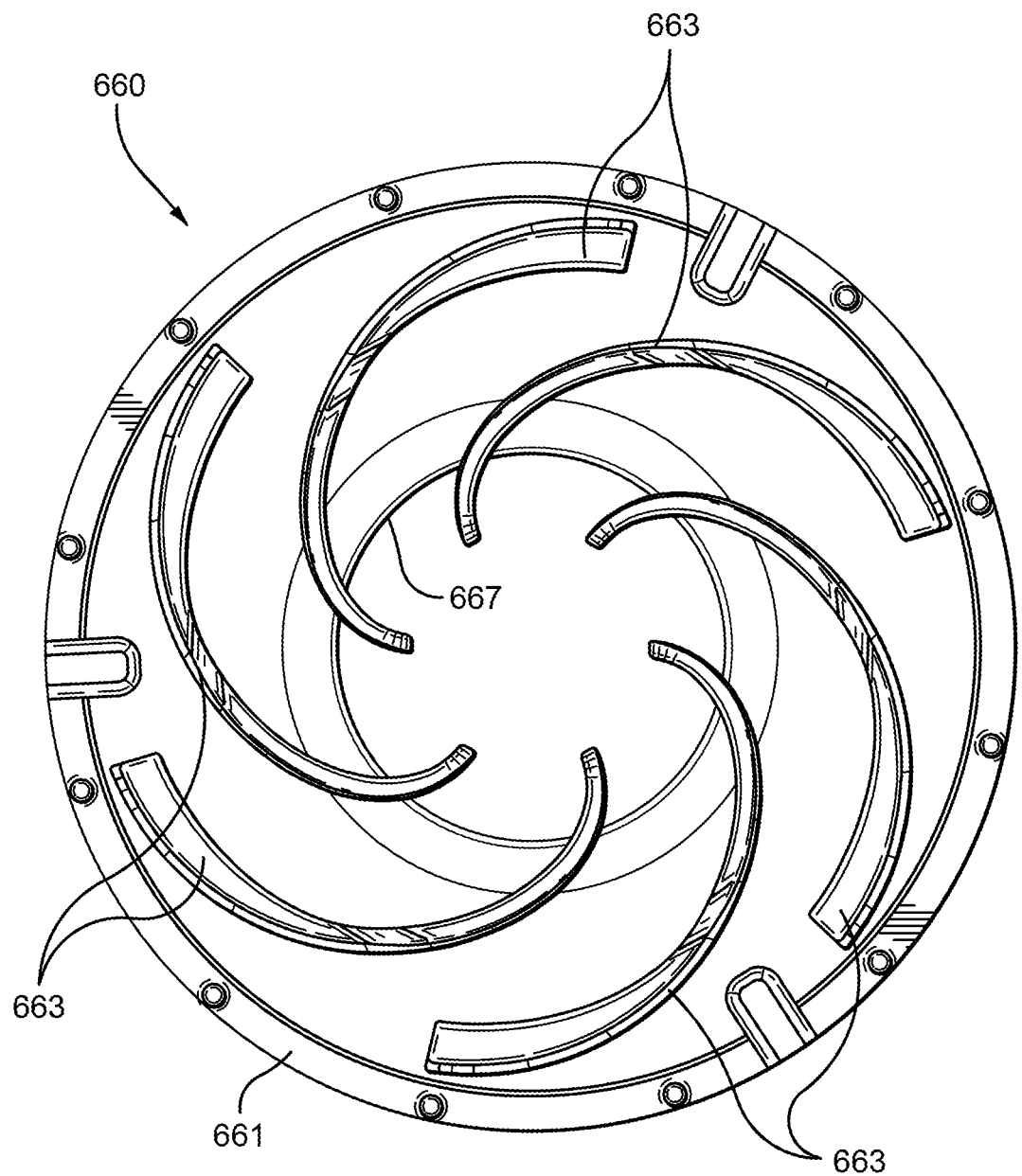

FIGS. 12-1 to 12-3 illustrate a blower 1010 according to another embodiment of the present invention. Similar to the blowers described above, the blower 1010 includes two stages with one impeller 1050 positioned on one side of the motor 1040 and one impeller 1052 positioned on the other side of the motor 1040. Also, the blower 1010 has axial symmetry with both the inlet 1026 and outlet 1028 aligned with an axis of the blower 1010.

In this embodiment, the stator 1048 of the stator assembly includes a slotted configuration. As best shown in FIG. 12-3, the stator or lamination stack 1048 includes a ring-shaped main body 1048(1) and a plurality of stator teeth 1048(2), e.g., six stator teeth, extending radially inwardly from the main body 1048(1). The stator coils or windings 1046 are wound on respective teeth 1048(2) as shown in FIG. 12-2. The windings can be inserted from the inside via respective slot openings (spacing between teeth).

Similar to arrangements described above, the outer circumference of the main body 1048(1) includes a toothed configuration that is adapted to engage or interlock with the stator component 1030. In addition, one or more slots 1051 may be provided in the outer circumference of the main body 1048(1) to accommodate passage of respective wires from the windings 1046.

The remaining portions of the blower are similar to arrangements described above, e.g., housing 1020 with first and second housing parts 1022, 1024, "cage"-like stator component 1030 with bearing tube 1038, and first and second shields 1060, 1070.

12. Blower with Coreless Motor

Figures 7, 8, 9, 10, 11, 12, 13:
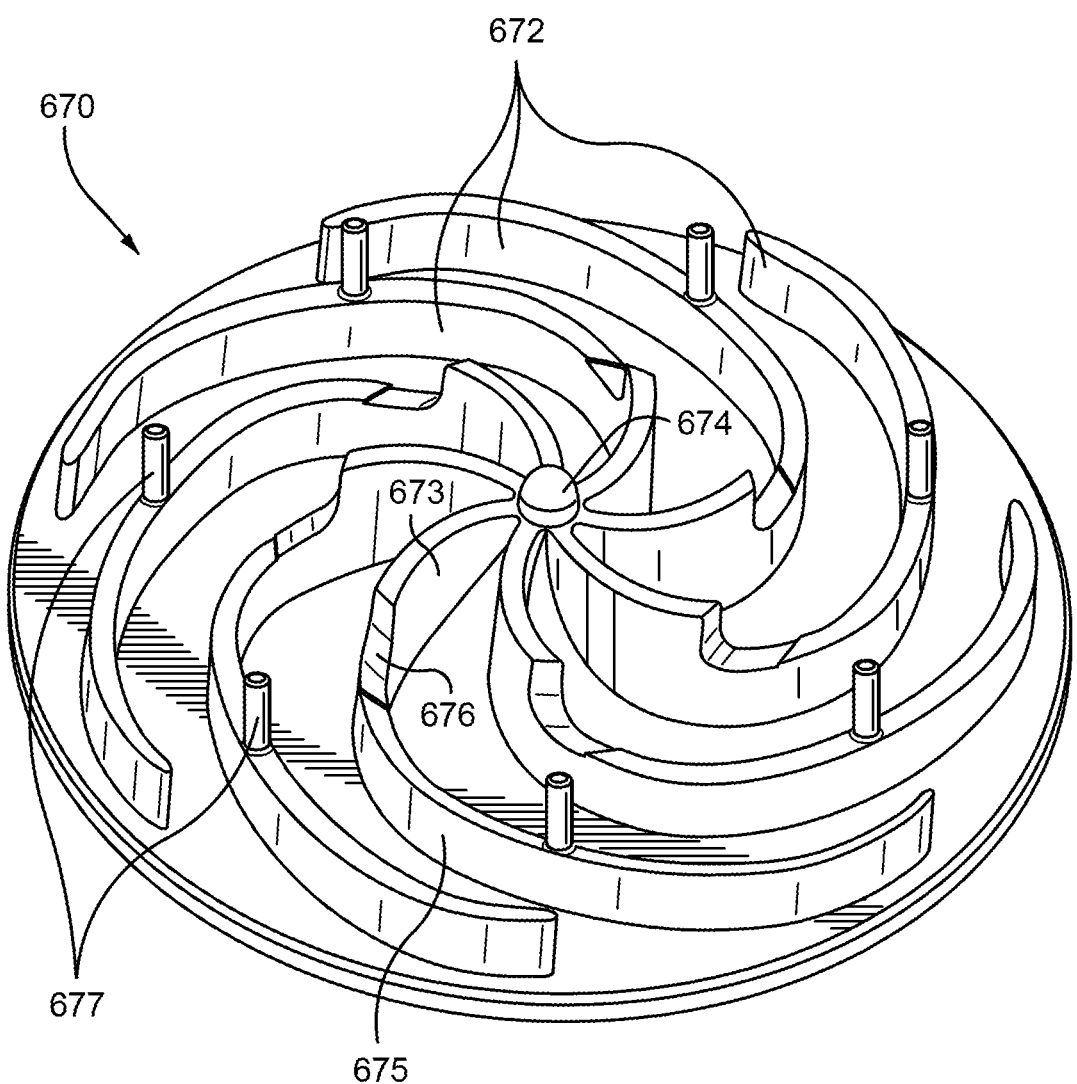
Figure 8:
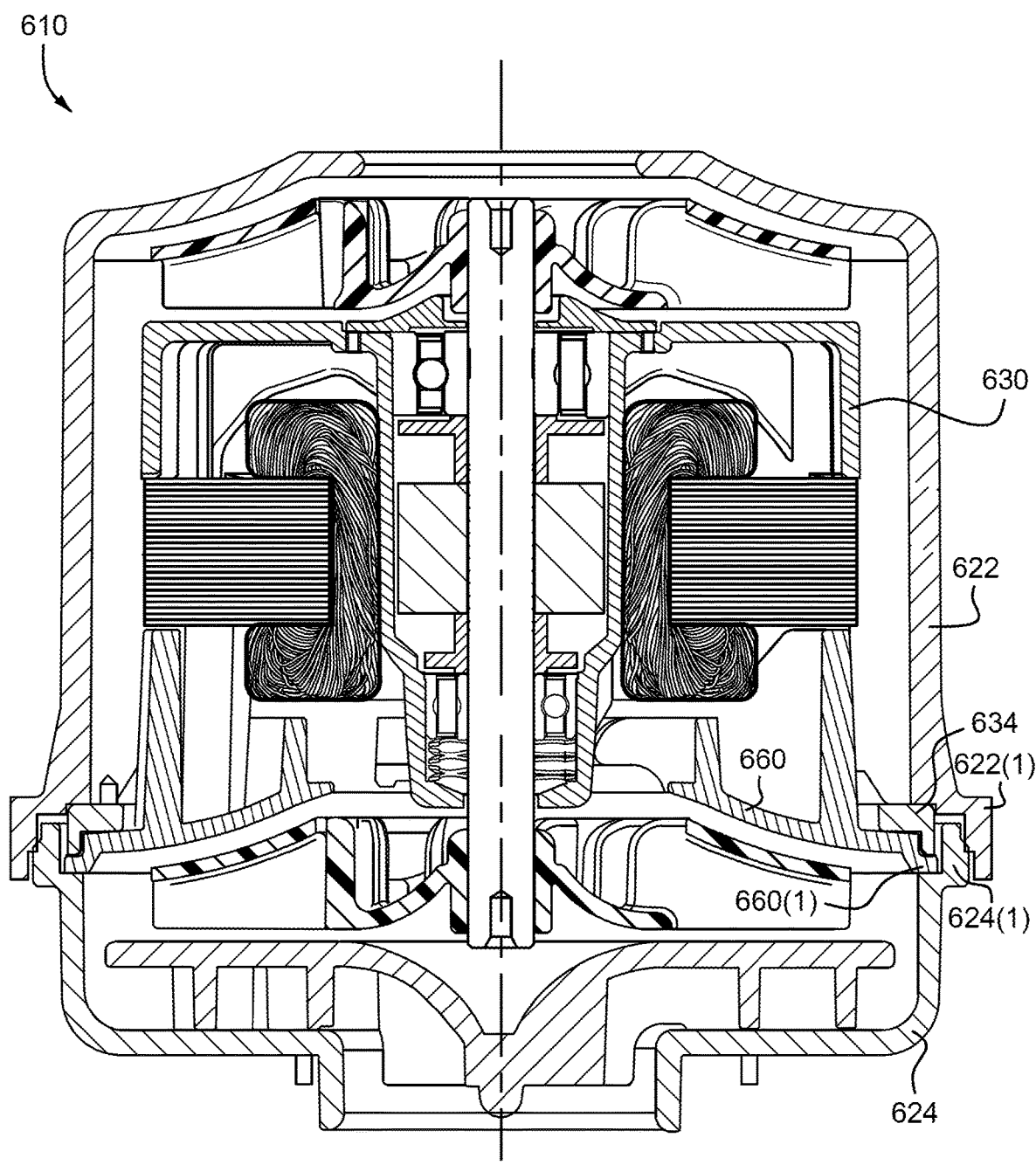
Figures 1, 9:
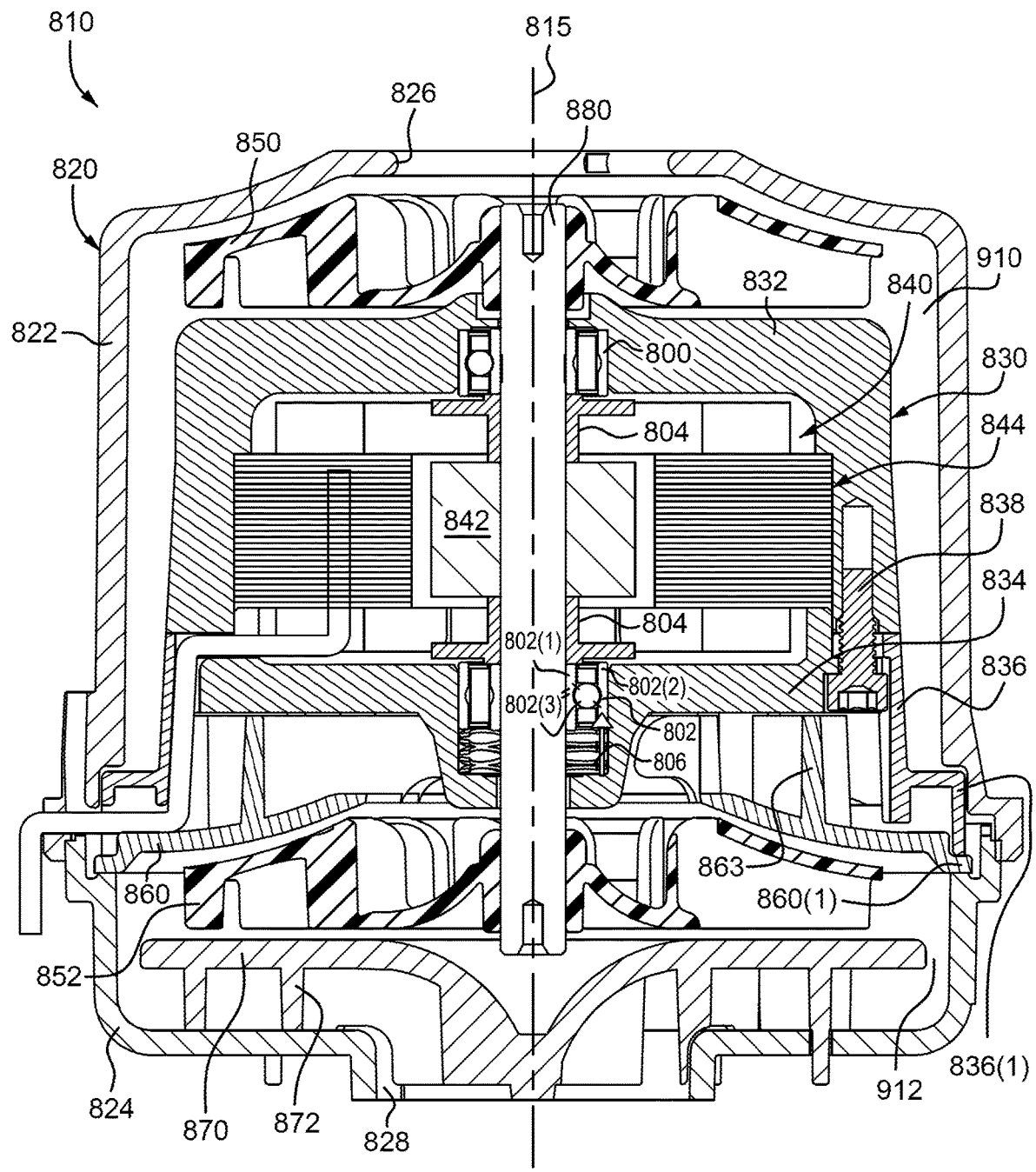
Figures 2, 9:
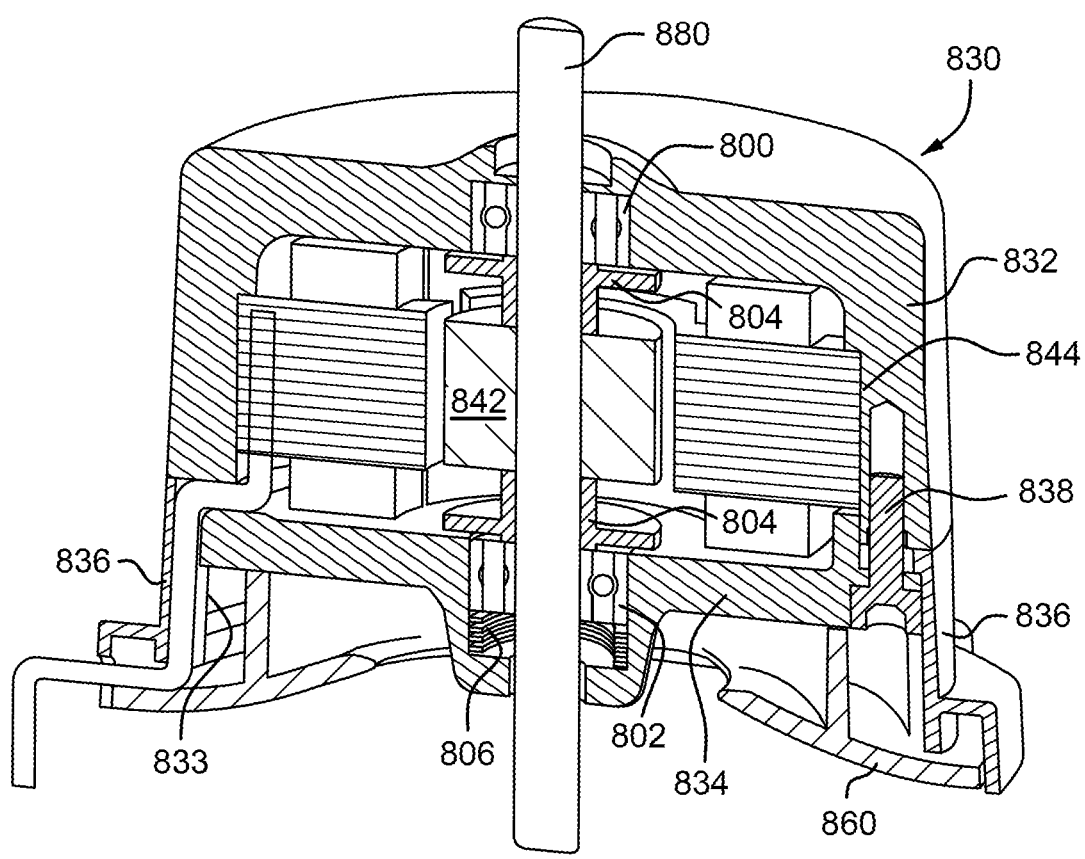
Figures 1, 10:
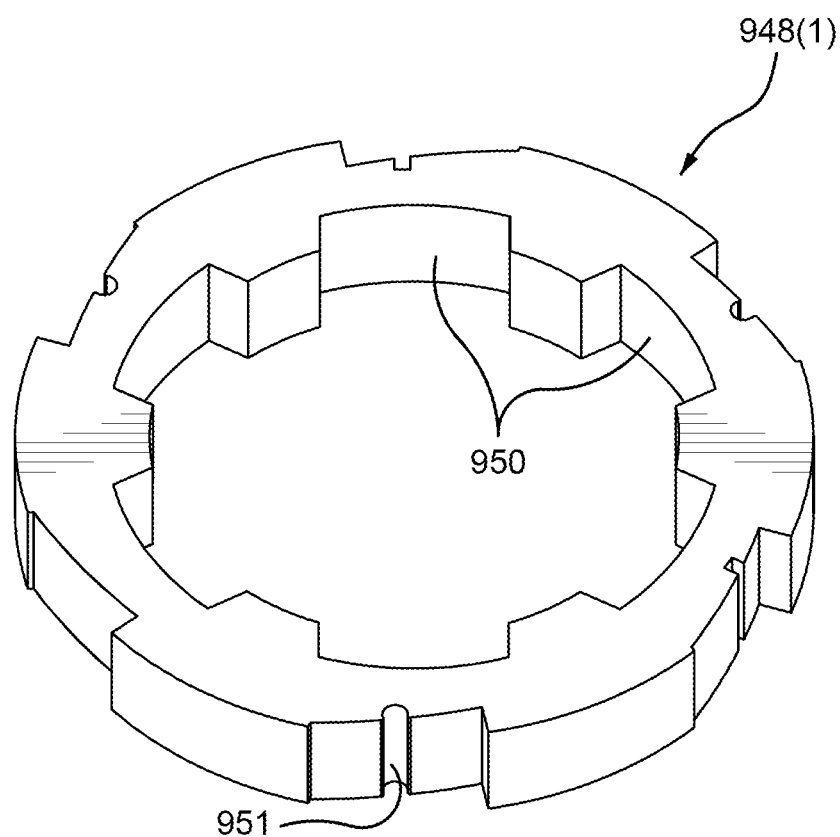
Figures 2, 10:
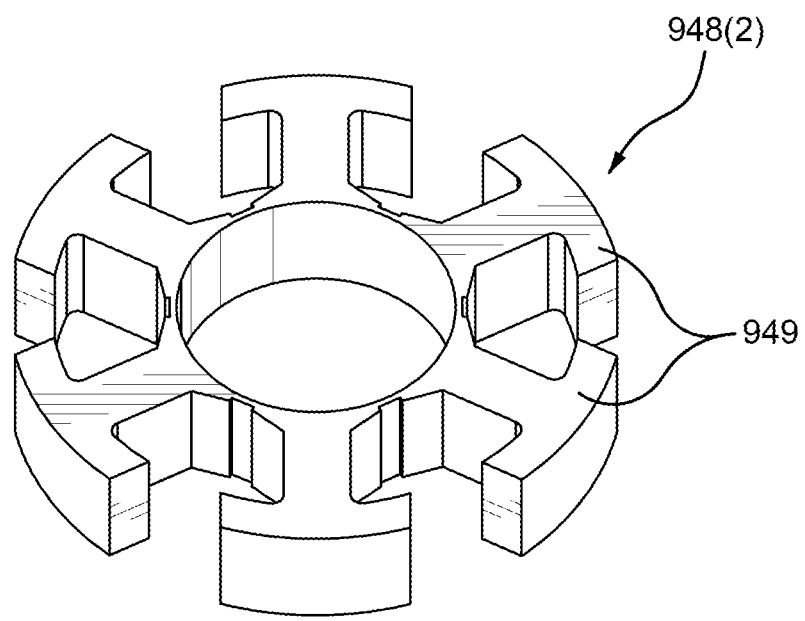
Figures 3, 10:
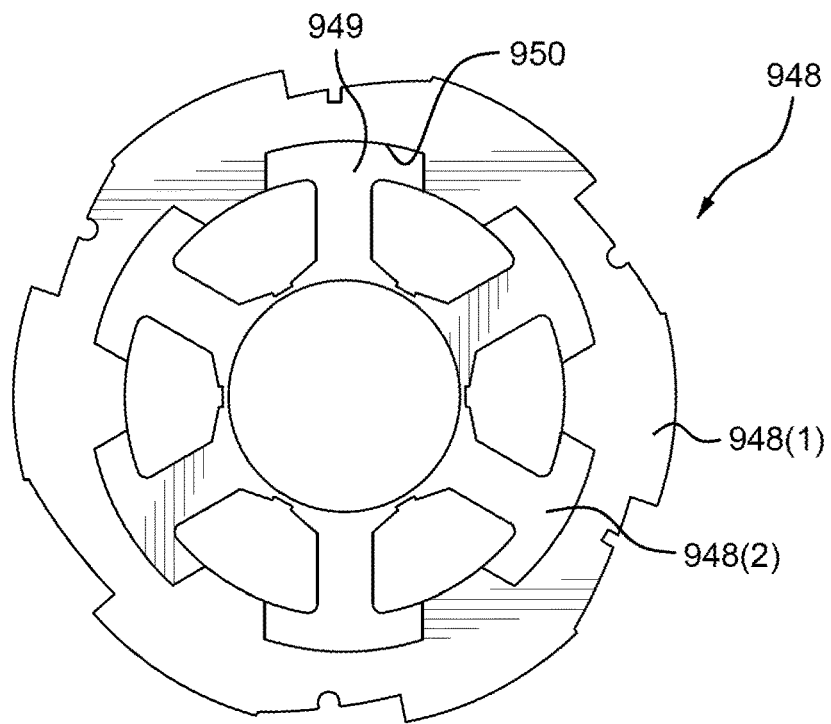
Figure 11:
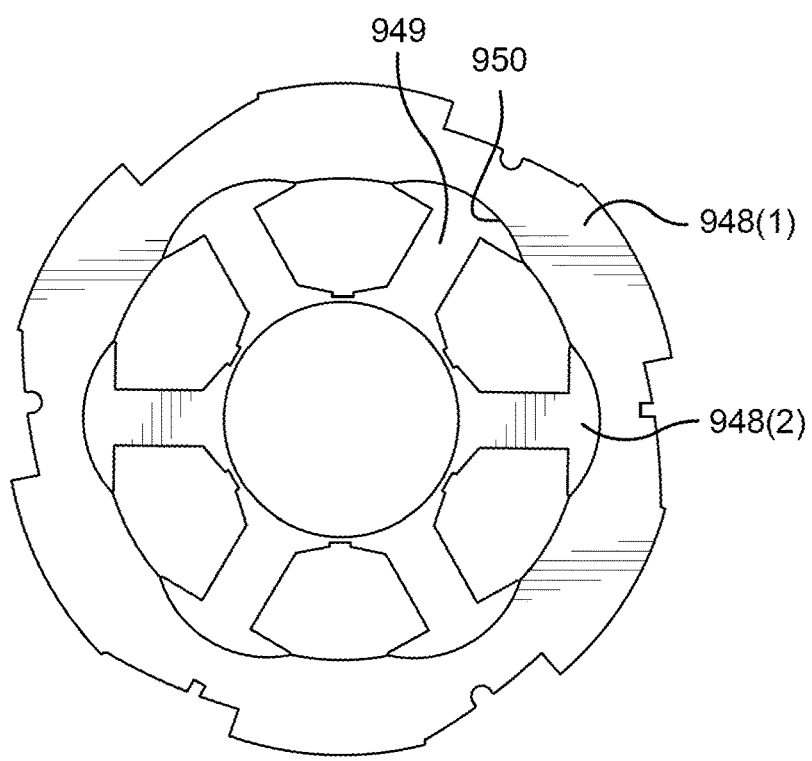
Figures 1, 12:
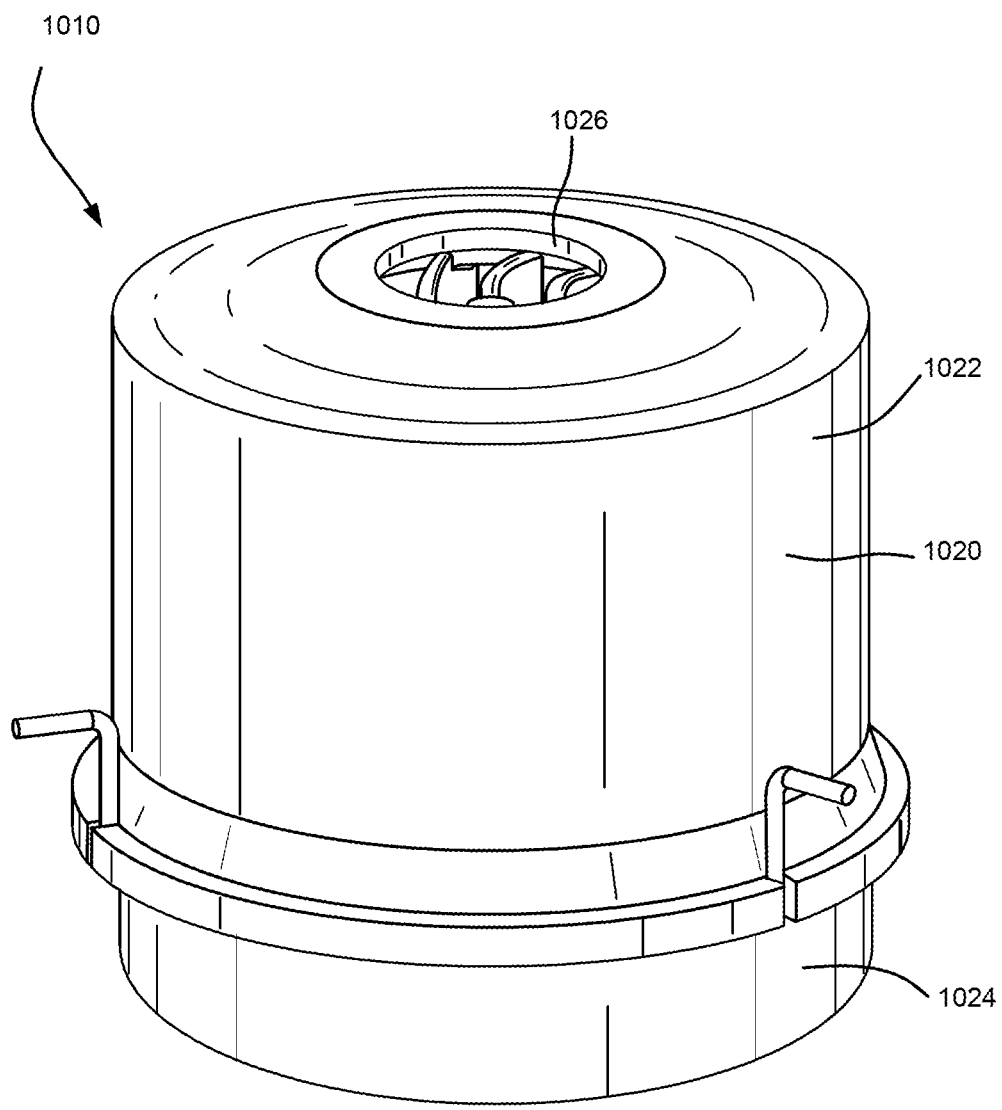
Figures 2, 12:
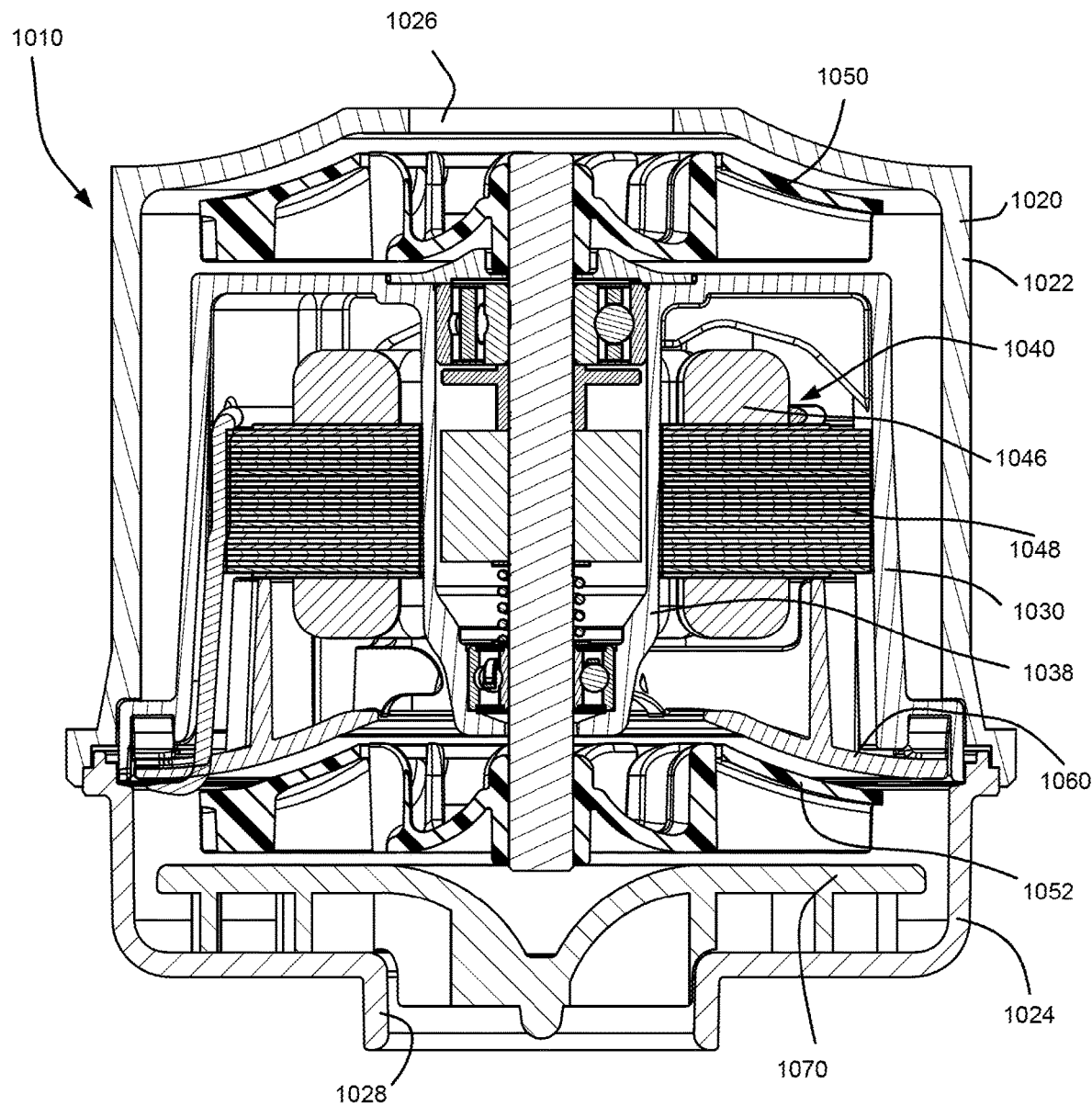
Figures 3, 12:
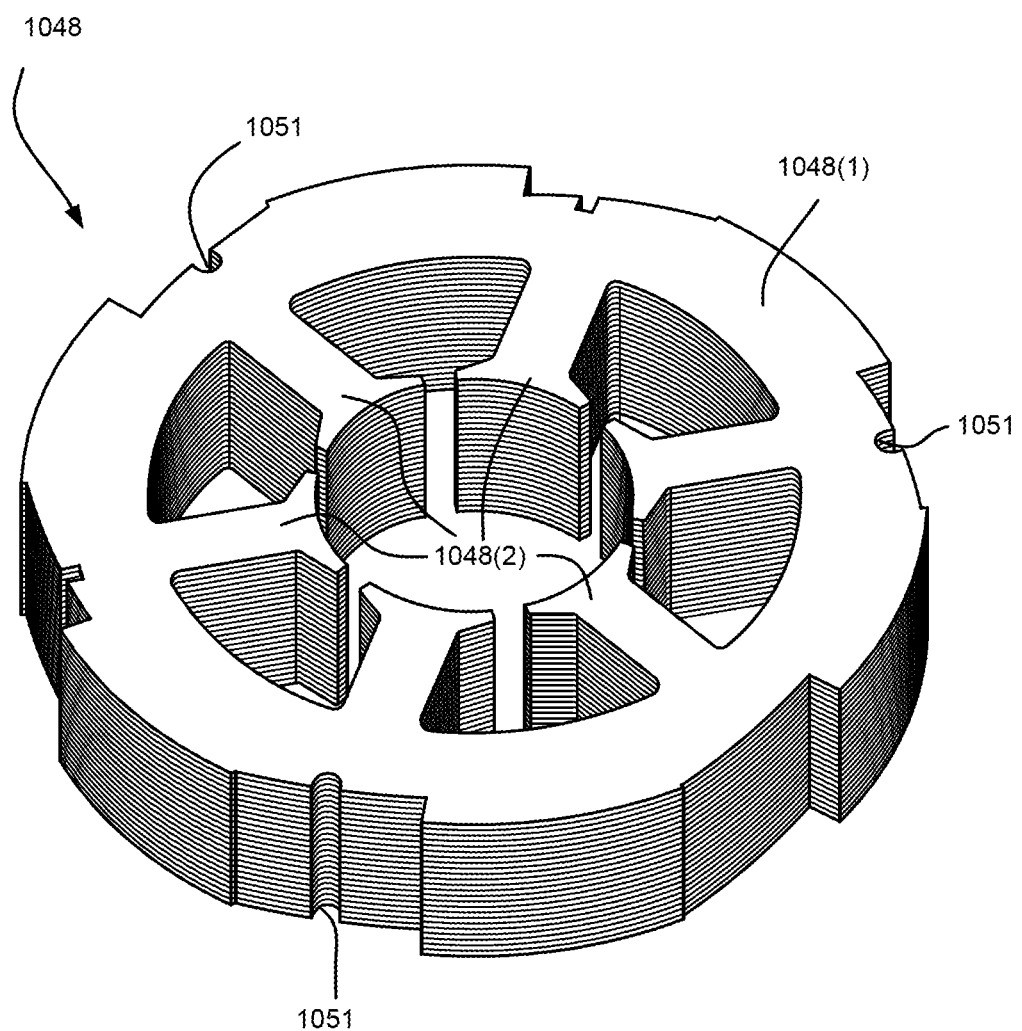
Figures 1, 13:
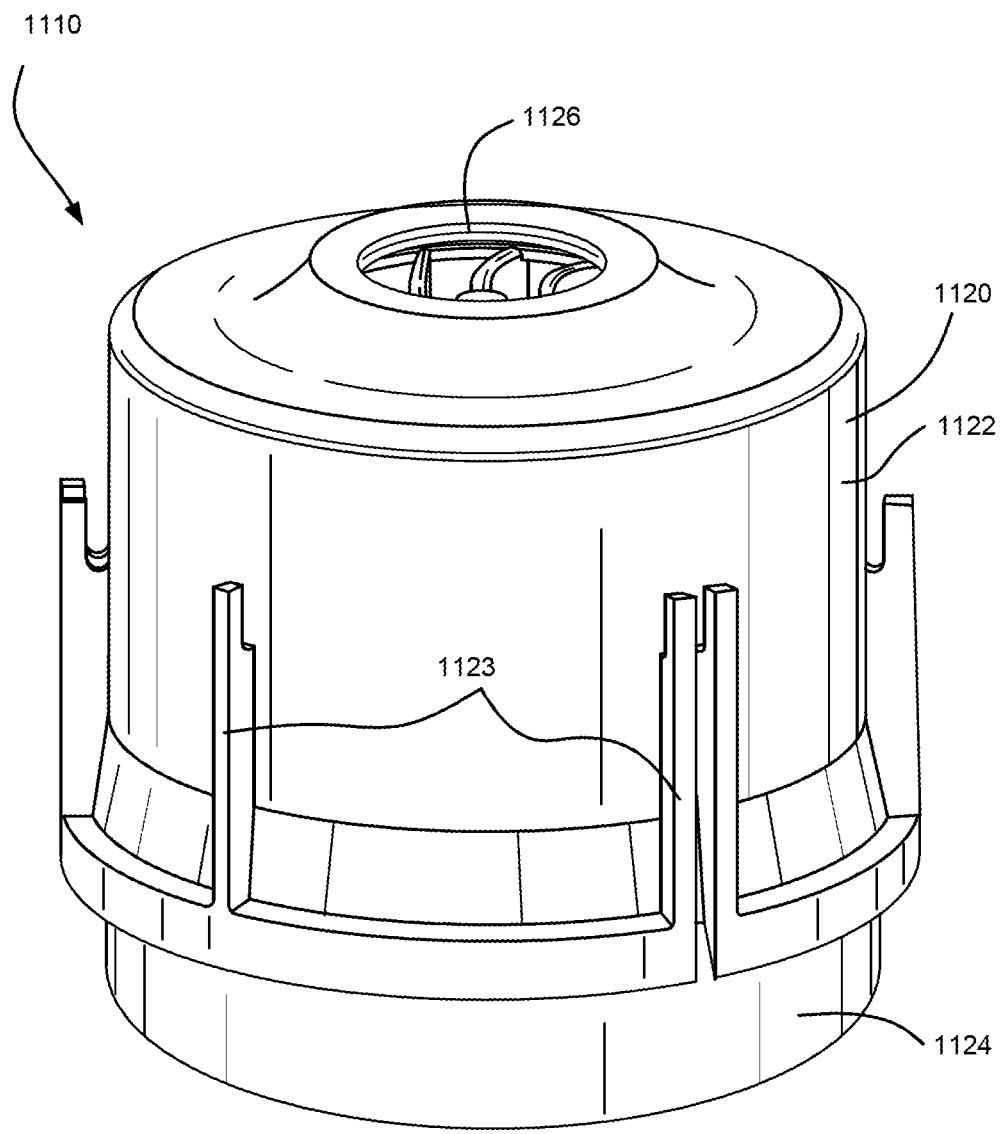
Figures 2, 13:
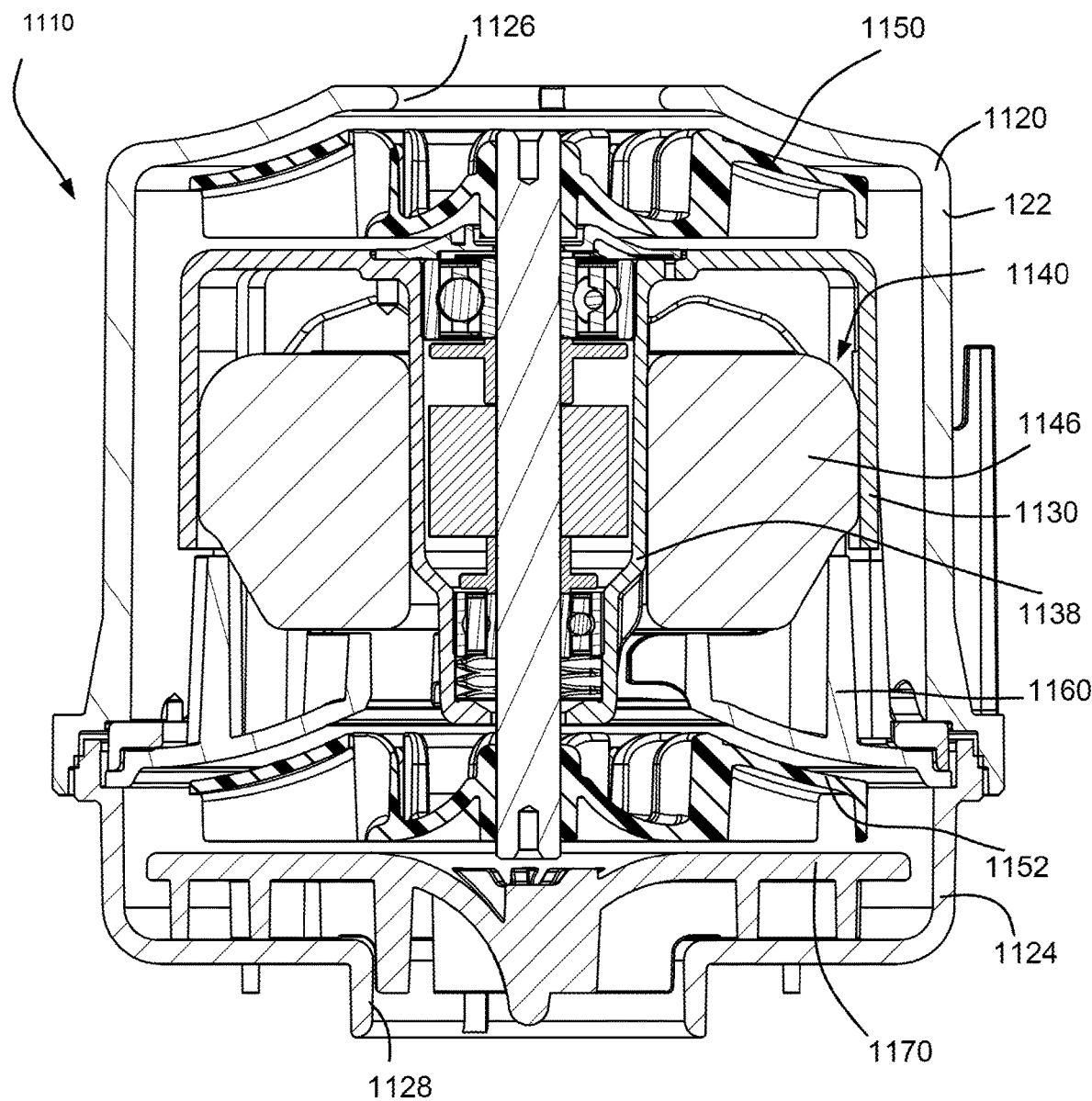

FIGS. 13-1 to 13-2 illustrate a blower 1110 according to another embodiment of the present invention. Similar to the blowers described above, the blower 1110 includes two stages with one impeller 1150 positioned on one side of the motor 1140 and one impeller 1152 positioned on the other side of the motor 1140. Also, the blower 1110 has axial symmetry with both the inlet 1126 and outlet 1128 aligned with an axis of the blower 1110.

In this embodiment, the blower 1110 includes a coreless motor in which the windings or magnet wire are wound directly on the stator component thereby eliminating a stator or lamination stack. For example, as best shown in FIG. 13-2, windings or magnet wire 1146 may be wound directly on the bearing tube 1138 of the stator component 1130. In an embodiment, the windings may be at least partially supported by side walls of the stator component.

The remaining portions of the blower are similar to arrangements described above, e.g., housing 1120 with first and second housing parts 1122, 1124, "cage"-like stator component 1130, and first and second shields 1160, 1170. In the illustrated embodiment, the first housing part 1122 may include one or more guide structures 1123 for guiding magnet wire outside the housing, e.g., binding post for looping wire.

13. Alternative Embodiments for Assembly

In an embodiment, the bearings supporting the shaft may be bonded to respective ends of the bearing tube by a plasma treatment stage. For example, with respect to the embodiment of blower 610, plasma may be used to treat the plastic surface of the first stage bearing seat of bearing tube 638 that engages the outer race of bearing 600. The plasma treatment allows the adhesive of choice (e.g., a Loctite cyanoacrylate compound) to wet nicely when applied. This wetting action has been shown to increase the bondline strength and also reduce the variation in that process (as determined by shear strength). The bondline holds the rotor assembly within the tube and stator assembly.

In an alternative embodiment, liquid primers may be used to treat the bearing seat before the adhesive (e.g., a Loctite cyanoacrylate compound) is applied. Also, an alternative to cyanoacrylate compound as an adhesive with the plasma/primers may be epoxy.

In an embodiment, the first and second housing parts of the housing may be bonded together with ultrasonic welding using a shear joint.

Also, in an embodiment, combinations of rigid and softer materials may be molded in a two-shot process (e.g., co-molding) to improve sealing in various positions through the blower.

In order to have the lead wires being the same length as they exit the blower housing, a "binding post" or "cleat" may be positioned on the outside of the housing. One or more wires may be looped around that binding post so that the lengths of the wires can be equalized.

In an embodiment, a labyrinth seal may be provided to allow the pressure to equalize between the outboard side of the first-stage bearing and the outboard side of the second-stage bearing to the extent that it is possible with minimal recirculating flow beneath the first-stage impeller (e.g., see FIGS. 7-3 and 7-6).

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A positive airway pressure device for generating a supply of pressurized gas to be provided to a patient for treatment, the positive airway pressure device comprising:
    an outer casing;
    a blower including a housing having an inlet along an inlet side thereof and an outlet along an outlet side thereof, the inlet and the outlet being co-axially aligned,
        wherein the blower is configured to draw a supply of gas into the housing through the inlet and provide a pressurized flow of gas at the outlet; and
    a support system comprising an annular seal and multiple feet between the blower and the outer casing,
        wherein the annular seal is provided to an outer surface of the housing and adapted to engage the outer casing to support the blower within the outer casing and separate the inlet side of the blower from the outlet side of the blower, and
        wherein the multiple feet are provided to a bottom of the blower and adapted to engage a base of the outer casing.

2. The positive airway pressure device according to claim 1, wherein the annular seal is overmolded onto the outer surface of the housing.

3. The positive airway pressure device according to claim 1, wherein the annular seal is formed as a separate piece adapted to be attached to the outer surface of the housing.

4. The positive airway pressure device according to claim 1, wherein the annular seal is molded of an elastomeric material.

5. The positive airway pressure device according to claim 1, wherein the annular seal provides a seal between low and high pressure sides of the blower.

6. The positive airway pressure device according to claim 1, wherein the annular seal suspends the blower in the outer casing.

7. The positive airway pressure device according to claim 1, further comprising an outlet muffler volume on the outlet side of the blower defined between the annular seal and the outer casing, and an inlet muffler volume on the inlet side of the blower defined between the annular seal and the outer casing.

* * * * *